United States Patent [19]

Patchett et al.

[11] Patent Number: 4,839,357

[45] Date of Patent: Jun. 13, 1989

[54] RENIN INHIBITORS CONTAINING PHENYLALANYL-HISTIDINE REPLACEMENTS

[75] Inventors: Arthur A. Patchett, Westfield; William J. Greenlee, Teaneck; William H. Parsons, Rahway; Prasun K. Chakravarty, Edison, all of N.J.

[73] Assignee: Merck & Co., Inc., Rahway, N.J.

[21] Appl. No.: 102,203

[22] Filed: Oct. 2, 1987

[51] Int. Cl.⁴ .................. A61K 31/16; A61K 31/18; A61K 31/41; A61K 31/505; C07D 279/10; C07D 413/00; C07D 265/30; C07D 235/04; C07C 143/78; C07C 103/00; C07C 149/41; C07C 143/67

[52] U.S. Cl. .................. 514/235.8; 514/237.2; 544/58.2; 544/58.4; 544/131; 544/139; 544/159; 548/331; 564/88; 564/154; 564/162; 560/12; 558/254

[58] Field of Search ............ 530/317, 328, 329, 331; 514/235.8, 237.2; 544/58.2, 58.4, 131, 139; 548/331; 564/88, 154, 162; 560/12; 558/258

[56] References Cited

U.S. PATENT DOCUMENTS

| | | | |
|---|---|---|---|
| 4,477,440 | 10/1984 | Boger et al. | 530/329 |
| 4,477,441 | 10/1984 | Boger et al. | 530/329 |
| 4,479,941 | 10/1984 | Veber et al. | 530/328 |
| 4,485,099 | 11/1984 | Boger et al. | 530/318 |
| 4,665,052 | 5/1987 | Boger | 530/317 |
| 4,665,055 | 5/1987 | Evans | 530/331 |
| 4,668,663 | 5/1987 | Boger | 530/329 |
| 4,668,770 | 5/1987 | Boger et al. | 530/329 |

*Primary Examiner*—Delbert R. Phillips
*Attorney, Agent, or Firm*—Frank S. Chow; Hesna J. Pfeiffer

[57] ABSTRACT

Peptides of the formula:

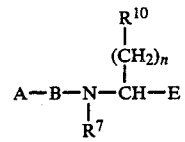

which comprise novel elements replacing the Phe(8)-His(9) sequence in renin-inhibitory peptides based on substrate analogy, which inhibit the substrate-cleaving action of renin and have improved bioavailability; compositions containing these renin-inhibitory peptides, optionally with other antihypertensive agents; and methods of treating hypertension or congestive heart failure or of establishing renin as a causative factor in these problems which employ the novel peptides.

5 Claims, No Drawings

RENIN INHIBITORS CONTAINING PHENYLALANYL-HISTIDINE REPLACEMENTS

The present invention is concerned with novel peptides which inhibit the angiotensinogen-cleaving action of the proteolytic enzyme, renin, with pharmaceutical compositions containing the novel peptides of the present invention as active ingredients, and with methods of treating hypertension and congestive heart failure and methods of diagnosis which utilize the novel peptides of the present invention.

BACKGROUND OF THE INVENTION

Renin is an endopeptidase (molecular weight about 40,000) produced and secreted by the juxtaglomerular cells of the kidney. Renin has a high specificity for and cleaves the naturally-occurring plasma glycoprotein, angiotensinogen, at only the 10, 11 peptide bond, i.e., between the 10th (Leu) and 11th (Leu) amino acid residues in the equine substrate, as described by Skeggs et al, *J. Exper. 26ed.* 1957, 106, 439, or between Leu 10 and Val 11 in the human renin substrate, as elucidated by Tewksbury et al., *Circulation* 59, 60, Supp. II: 132, October 1979.

This cleavage of its tetradecapeptide substrate, angiotensinogen, splits off the hemodynamically-inactive decapeptide, angiotensin I, which is converted in the lungs, kidney or other tissue by angiotensin-converting enzyme (ACE) to the potent pressor octapeptide, angiotensin II. Angiotensin II then causes constriction of the arterioles and is also believed to stimulate release of th sodium-retaining hormone, aldosterone, from the adrenal gland, thereby causing a rise in extracellular fluid volume. Thus, the renin-angiotensin system plays an important role in normal cardiovascular homeostasis and in some forms of elevated blood pressure (hypertension).

Inhibitors of angiotensin I converting enzyme have proven useful in the modulation of the renin-angiotensin system. Consequently, specific inhibitors of the catalytic and rate-limiting enzymatic step that ultimately regulates angiotensin II production, the action of renin on its substrate, have also been sought as effective investigative tools, as well as therapeutic agents in the treatment of hypertension and congestive heart failure.

Renin antibody, pepstatin (another aspartic proteinase, like renin), phospholipids, and substrate analogs, including tetrapeptides and octa- to tridecapeptides, with inhibition constants ($K_i$) in the $10^{-3}$ to $10^{-6}$M region, have been studied.

Umezawa et al., in *J. Antibiot. (Tokyo)* 23: 259-262, 1970, reported the isolation of a peptide, pepstatin, from actinomyces that was an inhibitor of aspartyl proteases such as pepsin, cathepsin D, and renin. Gross et al., *Science* 175: 656, 1972, reported that pepstatin reduces blood pressure in vivo after the injection of hog renin into nephrectomized rats. However, pepstatin has not found very wide application as an experimental agent because of its limited solubility and its inhibition of a variety of other acid proteases in addition to renin.

Many efforts have been made to prepare a specific renin inhibitor based on pig renin substrate analogy, since such analogy has been shown to correlate well with and predict human renin inhibitor activity. The octapeptide amino acid sequence extending from histidine-6 through tyrosine-13

```
  6    7    8    9   10   11   12   13
(—His—Pro—Phe—His—Leu—Leu—Val—Tyr—)
``` has been shown to have kinetic parameters essentially the same as those of the full tetradecapeptide renin substrate.

Kokubu et al., *Biochem. Pharmacol.*, 22, 3217-3223, 1973, synthesized a number of analogs of the tetrapeptide found between residues 10 to 13, but while inhibition could be shown, inhibitory constants were only of the order of $10^{-3}$M. Analogs of a larger segment of renin substrate have been also synthesized, e.g., Burton et al., *Biochemistry* 14: 3892-3898, 1975, and Poulsen et al., *Biochemistry* 12: 3877-3882, 1973, but a lack of solubility and weak binding (large inhibitory constant) generally resulted.

Modifications to increase solubility soon established that the inhibitory properties of the peptides are markedly dependent on the hydrophobicity of various amino acid residues. These modifications also established that increasing solubility by replacing lipophilic amino acids with hydrophilic isosteric residues can become counterproductive. Other approaches to increasing solubility have also had limited success.

Modifications designed to increase binding to renin have also been made, but here too, with mixed results.

A series of inhibitors of renin have been disclosed which contain the unnatural amino acid, statine: see, e.g., Veber et al, U.S. Pat. Nos. 4,384,994 and 4,478,826; Evans et al, U.S. Pat. No. 4,397,786; Boger et al, *Nature*, 1983, 303, 81-84 and U.S. Pat. Nos. 4,470,971; 4,485,099; 4,663,310 and 4,668,770; Matsueda et al, EP-A 128 762, 152 255; Morisawa et al., EP-A 186 977; Riniker et al, EP-A 111 266; Bindra et al, EP-A 155 809; Stein et al, *Fed. Proc.* 1986, 45, 869; and Hölzemann et al, German Offenlegungsschrift DE No. 3438545. Attempting to explain the effect of statine, by Powers et al., in *Acid Proteases, Structure, Function and Biology*, Plenum Press, 1977, 141-157, observed that in pepstatin, statine occupies the space of the two amino acids on either side of the cleavage site of a pepsin substrate and by Tang et al., in *Trends in Biochem. Sci.*, 1: 205-208 (1976) and *J. Biol. Chem.*, 251: 7088-94, 1976, pointed out that the statine residue of pepstatin resembles the transition state for pepsin hydrolysis of peptide bonds.

Renin inhibitors containing other peptide bond isosteres, including a reduced carbonyl isostere have been disclosed by M. Szelke et al, in work described in published European patent application Nos. 45 665 and 104 041; in U.S. Pat. No. 4,424,207, and in PCT Int. Appl. WO 84/3044; in *Nature*, 299, 555 (1982); *Hypertension*, 4, Supp. 2, 59, 1981; and British Pat. No. 1,587,809. In *Peptides, Structure and Function: Proceedings of the Eighth American Peptide Symposium*, ed. V. J. Hruby and D. H. Rich, p. 579, Pierce Chemical Co., Rockford, IL, 1983, Szelke et al also showed isosteric substitutions at the Leu-Leu site of cleavage, resulting in compounds with excellent potency.

Other peptide bond isosteres have then been disclosed in Buhlmayer et al in EP-A 144 290 and 184 550; Hester et al, EP-A 173 481; Raddatz, EP-A 161 588; Dann et al, *Biochem. Biophys, Res. Commun.* 1986, 134, 71-77; Fuhrer et al, EP-A 143 746; Kamijo et al, EP-A 181 110; Thaisrivongs et al, *J. Med. Chem.*, 1985, 28, 1553-1555; Ryono et al., EP-A 181 071; and Evans et al, U.S. Pat. No. 4,609,641.

Other modifications which have been tried include preparing renin inhibitors with non-peptide C-termini, such as disclosed in European Published Applications 172 346 and 172 347; Evans et al, *J. Med. Chem.*, 1985, 28, 1755-1756; and Bock et al, *Peptides, Structure and Function: Proceedings of the Ninth American Peptide Symposium*, ed. C. M. Deber et al, pp. 751-754, Pierce Chemical Co., Rockford, IL, 1985. Kokubu et al, in *Hypertension*, 1985, 7, Suppl. I, p. 8-10 and Matsueda et al, in *Chemistry Letters*, 1985, 1041-1044 and in European Published Applications 128 762 and 152 255 disclosed peptide aldehyde renin inhibitors, and Hanson et al in *Biochem. Biophys. Res. Commun.* 1985, 132, 155-161, reported peptide glycol inhibitors.

These various renin inhibitors all generally comprise peptide-based inhibitors in which a sequence of the type: ... A-B-D-E-F-G-J-K-L ..., where G is a peptide bond mimic and A,B,D,E,F,J,K, and L may individually be absent or may represent naturally-occuring or modified amino acids. Typical sequences of this type include:

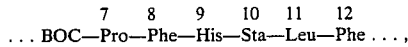

... BOC—Pro—Phe—His—Sta—Leu—Phe ... , 7    8    9   10   11   12 or

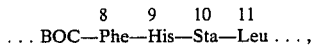

... BOC—Phe—His—Sta—Leu ... , 8    9   10   11 where the N-terminus typically comprises an amino acid protecting group such as BOC or CBZ, and the N-terminal amino acids are Pro-Phe-His or Phe-His.

Replacements for the Phe(8)-His(9) portion of these sequences have been described among these references, wherein other aromatic amino acids (Tyr, Trp, etc) or substituted aromatic amino acids are generally mentioned as replacements for Phe. Then, other amino acids (e.g., Lys, Leu) have been suggested as replacements for His, or amino acids of the form, $NH_2$—CH(CH$_2$Het)CO$_2$H, wherein "Het" is a mono- or bicyclic heterocycle, have been substituted for either His or Phe. These 8-9-substituted sequences include peptides in which various peptide bonds have been N-methylated or reduced in order to stabilize the resulting inhibitor against enzymatic degradation. Otherwise, however, no advantage in renin-inhibitory potency or in pharmacological properties has been demonstrated or suggested by making such substitutions for the Phe-His sequence.

DESCRIPTION OF THE INVENTION

The present invention discloses renin inhibitors demonstrating improved bioavailability, in which a novel element, which may comprise a single component, or may consist of a novel component linked to histidine or a known histidine substitute, replacing the Phe(8)-His(9) N-terminal sequence, is combined with statine or other peptide bond isostere.

In particular, the present invention is directed to renin-inhibitory peptides of the formula:

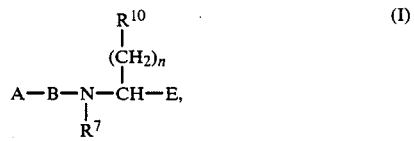

(I)

wherein
A is:

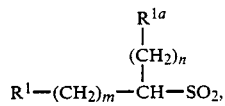

where
$R^1$ and $R^{1a}$ are independently hydrogen; aryl, wherein aryl is unsubstituted or mono-, di- or trisubstituted phenyl or naphthyl, where the substituent(s) is-/are independently selected from the group consisting of $C_1$-$C_7$-alkyl, amino, mono- or di-$C_1$-$C_4$-alkylamino, amino-$C_1$-$C_4$-alkyl, hydroxy-$C_1$-$C_4$-alkyl, mono- or di-$C_1C_4$-alkyamino-$C_1$-$C_4$-alkyl, guanidyl, guanidyl-$C_1$-$C_4$-alkyl, hydroxyl, $C_1$-$C_4$-alkoxy, $CF_3$, halo, CHO, $CO_2H$, $CO_2$-$C_1$-$C_4$-alkyl, $-CONH_2$, $-CONH$-$C_1$-$C_4$-alkyl, $NR^5R^6$, and $N(R^5)_3 \oplus A\ominus$, wherein $R^5$ and $R^6$ are independently hydrogen, unsubstituted or monosubstituted $C_1$-$C_4$-alkyl, where the substituent is amino, $C_1$-$C_4$-alkylamino, $C_1$-$C_4$-dialkylamino, hydroxyl, $C_1$-$C_4$-alkoxy or $N(C_1$-$C_4$-alkyl)$_3\oplus A\ominus$; and $A\ominus$ is a counterion selected from the group consisting of single negatively-charged ions, such as chloride, bromide, nitrate, perchlorate, benzoate, maleate, benzene sulfonate, tartrate, hemitartrate and acetate; $C_1$-$C_4$-alkyl; $C_3$-$C_7$-cycloalkyl; amino; hydroxyl; thiol; mono- or di-$C_1$-$C_4$-alkylamino; halo; $CO_2H$; $CO_2$-$C_1$-$C_4$-alkyl; $CONR^5R^6$, wherein $R^5$ and $R^6$ are as defined above; $C_1$-$C_4$-alkoxy; or Het, wherein Het is an unsubstituted or mono- or disubstituted 5-, 6- or 7-membered heterocyclic ring or benzofused 5-, 6-, or 7-membered heterocyclic ring, where the one or two heteroatoms are independently selected from the group consisting of N, O, S, NO, SO, SO$_2$ or quaternized N, and the substituent(s) is/are independently selected from the group consisting of hydroxyl, thiol, $C_1$-$C_6$-alkyl, $CF_3$, $C_1$-$C_4$-alkoxy, halo, aryl, aryl-$C_1$-$C_4$-alkyl, amino, mono- or di-$C_1$-$C_4$-alkylamino, amino-$C_1$-$C_4$-alkylamino, amino-$C_1$-$C_4$-alkyl, hydroxy-$C_1$-$C_4$-alkyl, di-$C_1$-$C_4$-alkylamino-$C_1$-$C_4$-alkyl, guanidyl, guanidyl-$C_1$-$C_4$-alkyl, CHO, $CO_2H$, $CO_2$-$C_1$-$C_4$-alkyl, $NR^5R^6$, and $N(R^5)_3\oplus A\ominus$ wherein $R^5$, $R^6$ and $A\ominus$ are as defined above;

m is 0-to-3;
n is 0-to-3;

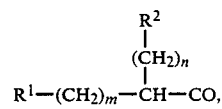

where
$R^1$, m and n are as defined above; and
$R^2$ is Het, as defined above; except that when $R^1$ is amino, hydroxyl, or mono- or di-$C_1$-$C_4$-alkylamino, m cannot be 0;
$R^{2a}X$,
where
$R^{2a}$ is aryl, as defined above, or Het, as defined above; and
X is CO, SO$_2$, or CH—OH;

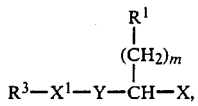

where
R³ is OR⁴, where R⁴ is $C_1$-$C_4$-alkyl or aryl-$C_1$-$C_2$-alkyl; aryl, as defined above; Het, as defined above; or NR⁵R⁶, wherein R⁵ and R⁶ are as defined above;
X¹ is CO, SO₂ or $$\begin{matrix} O & & O \\ \| & & \| \\ S-NH-C; \\ \| \\ O \end{matrix}$$

Y is CH₂ or O; and
R¹, X and m are as defined above; except that:
when X and X¹ are both CO, then Y cannot be O;
when X¹ is SO₂ and Y is CH₂ or O, then R¹-(CH₂)ₘ cannot equal hydrogen; or
when Y is O and R³ is OR⁴, X cannot be SO₂;

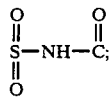

where
R¹, R¹ᵃ, X, m and n are as defined above, except that when X is CO, R¹-(CH₂)ₘ and R¹ᵃ-(CH₂)ₙ do not both equal $C_1$-$C_5$-alkyl;

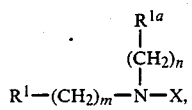

where
R¹ᵇ is aryl, as defined above; Het, as defined above; unsubstituted or monosubstituted $C_2$-$C_6$-straight or branched-chain alkyl or $C_3$-$C_7$-cycloalkyl, wherein the substituent is amino, hydroxyl, thio, halo, or mono- or di-$C_1$-$C_4$-alkylamino; N($C_1$-$C_4$-alkyl)₃⊕A⊖, wherein A⊖ is as defined above; CO₂H; CONR⁵R⁶, wherein R⁵ and R⁶ are as defined above; or $C_1$-$C_4$-alkoxy;
Z is O, S, SO, SO₂ or NR⁷, wherein R⁷ is hydrogen or $C_1$-$C_4$-alkyl;
q is 0-to-2; and
R¹ᵃ, X, m and n are as defined above; except that when Z is O or NR⁷ and q is 0, then
m cannot equal 0 or 1, R¹ᵇ-(CH₂)ₘ cannot be hydrogen or $C_1$-$C_5$-alkyl, and
R¹ᵃ-(CH₂)ₙ cannot be hydrogen;
or

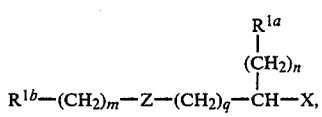

where
Y¹ is CH₂ or NR⁷, wherein R⁷ is as defined above; and
R¹ᵃ, R³, X and n are as defined above;
B is

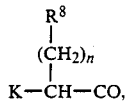

where
K is NR¹, wherein R¹ is as defined above; or CH₂;
R⁸ is unsubstituted or monosubstituted $C_1$-$C_4$-alkyl, wherein the substituent is carboxyl, amino, NHCOR¹, where R¹ is as defined above, hydroxyl, guanidino, $C_1$-$C_4$-alkoxycarbonyl, or thiol; Het, as defined above; or aryl, as defined above;
n is as defined above;

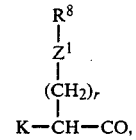

where
Z¹ is O, S, NR⁷, NR⁷—CO, CO-NR⁷, NR⁷SO₂, SO₂NR⁷, SO, or SO₂, wherein R⁷ is as defined above;
r is 1-to-3; and
K and R⁸ are as defined above; or
Z¹—R⁸ is alternatively X¹R³, wherein X¹ and R³ are as defined above;
or

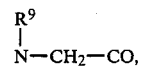

where
R⁹ is $C_1$-$C_4$-alkyl, substituted by R⁸ or Z—R⁸, wherein R⁸ and Z are as defined above;
R¹⁰ is —CHR¹¹R¹¹ᵃ,
where
R¹¹ and R¹¹ᵃ are related such that when R¹¹ is hydrogen; $C_1$-$C_5$-alkyl; aryl, as defined above; Het, as defined above; $C_1$-$C_3$-alkoxy; $C_1$-$C_3$-alkylthio; or unsubstituted or mono- or disubstituted $C_3$-$C_7$-cycloalkyl, wherein the substituent(s) is/are independently selected from the group consisting of $C_1$-$C_4$-alkyl, trifluoromethyl, hydroxy, $C_1$-$C_4$-alkoxy, and halo; then R¹¹ᵃ is hydrogen; or when R¹¹ is hydroxy-$C_1$-$C_4$-alkyl or amino-$C_1$-$C_4$-alkyl, then R¹¹ᵃ is hydrogen or $C_1$-$C_3$ alkyl;
n and R⁷ are as defined above; and
E is

where
W is OH, NH₂ or OR¹², wherein R¹² is $C_1$-$C_4$-alkanoyl or $C_1$-$C_6$-alkanoyloxy-$C_1$-$C_4$-alkyl; and
G is Q-CO-T-V,
wherein
Q is a single bond; CH—R¹³, where R¹³ is hydrogen; aryl, as defined above; $C_1$-$C_8$-alkyl; $C_3$-$C_7$-cycloalkyl; mono- or disubstituted $C_2$-$C_8$-alkyl, where the substituent(s) is/are independently selected from the group consisting of hydroxy; CO₂H; CO₂-$C_1$-$C_4$-alkyl; CONR⁵R⁶, wherein R⁵ and R⁶ are as defined above; amino; mono- or di-$C_1$-$C_4$- alkylamino; and guanidyl, and the substitution occurs on the last 1 or 2 carbon atoms of the alkyl chain; or mono- or disubstituted aryl or $C_3$-$C_7$-cycloalkyl, where the substituent(s) is/are independently selected from the group consisting of $C_1$-$C_4$-alkyl, trifluoromethyl, hydroxy, $C_1$-$C_4$-alkoxy, and halo; or $CH_2$—$CH$—$R^{13a}$, where $R^{13a}$ is $CHR^{14}R^{14a}$, wherein $R^{14}$ is hydrogen; amino; hydroxyl; $C_1$-$C_5$-alkyl; $C_3$-$C_7$-cycloalkyl; aryl, as defined above; aryl-$C_1$-$C_4$-alkyl; Het, as defined above; Het-$C_1$-$C_4$-alkyl; amino-$C_1$-$C_4$-alkyl; or guanidyl-$C_1$-$C_4$-alkyl; and $R^{14a}$ is hydrogen or $C_1$-$C_5$-alkyl;

T is absent or

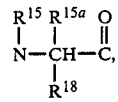

where $R^{15}$ and $R^{15a}$ are independently H or $C_1$-$C_4$-alkyl; and $R^{18}$ is —$(CH_2)_wNR^{19}R^{20}$, wherein $R^{19}$ and $R^{20}$ are independently hydrogen; Het, as defined above; aryl, as defined above; unsubstituted or monosubstituted $C_1$-$C_{C4}$-alkyl where the substituent is selected from the group consisting of aryl, as defined above, Het, as defined above, amino, hydroxyl, mono- or di-$C_1$-$C_4$-alkylamino, $CO_2H$, $SO_3H$ and $CONR^5R^6$, wherein $R^5$ and $R^6$ are as defined above; and w is 1-to-5; —$(CH_2)_xN(R^{19})_3 \oplus A^\ominus$, wherein x is 2-to-5 and $R^{19}$ and $A^\ominus$ are as defined above;

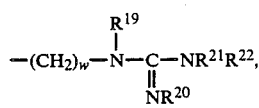

wherein $R^{21}$ and $R^{22}$ are independently chosen from the definitions of $R^{19}$, or $R^{21}$ and $R^{22}$ together are —$(CH_2)_4$— or —$(CH_2)_5$—, and $R^{19}$, $R^{20}$ and w are as defined above; or —$(CH_2)_w$—$N$=$CH$—$NR^{21}R^{22}$, wherein $R^{21},R^{22}$ and and w are as defined above; and V is $O$—$(CH_2)_uR^{16}$, where $R^{16}$ is hydrogen; aryl, as defined above; Het, as defined above; or unsubstituted or mono- or disubstituted $C_2$-$C_4$-alkyl, $C_3$-$C_7$-cycloalkyl or $C_2$-$C_7$-cycloalkyl-$C_1$-$C_4$-alkyl, wherein the substituent(s) is/are independently selected from the group consisting of amino, hydroxyl, $C_1$-$C_4$-alkoxy, thio, halo, mono- or di-$C_1$-$C_4$-alkylamino, $CO_2H$, or $CONR^5R^6$, where $R^5$, $R^6$ and $A^-$ are as defined above; and u is 0-to-5;

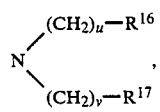

where $R^{17}$ is hydrogen; aryl, as defined above; Het, as defined above; unsubstituted or mono- or disubstituted $C_2$-$C_4$-alkyl, $C_3$-$C_7$-cycloalkyl or $C_3$-$C_7$-cycloalkyl-$C_1$-$C_4$-alkyl, wherein the substituent(s) is/are independently selected from the group consisting of amino; hydroxyl; $C_1$-$C_4$-alkoxy; thio; halo; mono- or di-$C_1$-$C_4$-alkylamino; $CO_2H$; quanidino; mono-, di- or tri-$C_1$-$C_4$-alkylguanidino; —$N(R^5)_3 \oplus A^\ominus$ and $CONR^5R^6$, where $R^5$, $R^6$ and $A^\ominus$ are as defined above; v is 0-to-5; and $R^{16}$ and u are as defined above; or $R^{16}$ and $R^{17}$ are joined to form an unsubstituted or mono- or disubstituted 5- to 7-membered heterocyclic ring or benzofused 5- to 7-membered heterocyclic ring, which is either saturated or unsaturated, wherein the one to three heteroatoms is/are independently selected from the group consisting of nitrogen, oxygen and sulfur, and the substituent(s) is/are independently selected from the group consisting of $C_1$-$C_6$-alkyl; hydroxyl; trifluoromethyl; $C_1$-$C_4$-alkoxy; halo; aryl, as defined above; aryl-$C_1$-$C_4$-alkyl; amino; thio; and mono- or di-$C_1$-$C_4$-alkylamino;

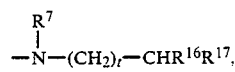

where t is 0-to-2 and $R^7$, $R^{16}$ and $R^{17}$ are as defined above, or $R^{16}$ and $R^{17}$ are joined as defined above; or $O$—$CHR^{16}R^{17}$, where $R^{16}$ and $R^{17}$ are as defined above, or are joined as defined above;

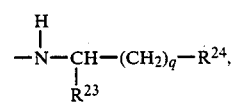

where $R^{23}$ is hydrogen, $C_1$-$C_4$-alkyl, or aryl-$C_1$-$C_4$-alkyl, wherein aryl is as defined above; $R^{24}$ is Het, as defined above; —$NR^{19}R^{20}$, —$N(R^{19}R^{20}R^{21}) \oplus A^\ominus$,

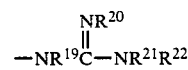

or —$N$=$CH$—$NR^{19}R^{20}$, wherein $R^{19}$, $R^{20}$, $R^{21}$, $R^{22}$ and $A^\ominus$ are as defined above; —$CO_2H$; —$SO_3H$; aryl, as defined above; and when q is not equal to 0, is also alternatively di-$C_1$-$C_4$-alkylamino: and q is as defined above;

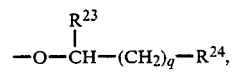

where $R^{23}$, $R^{24}$ and q are as defined above; —$N(CH_2CH_2)_2N$—$R^{19}$, where $R^{19}$ is as defined above; —$N(CH_2CH_2)_2NR^{19}R^{20} \oplus A^\ominus$, where $R^{19}$, $R^{20}$ and $A^\ominus$ are as defined above; —NH-Het, where Het is as defined above;

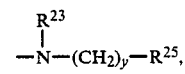

where $R^{25}$ is Het, as defined above; aryl, as defined; $C_1$-$C_4$-alkyl; and when y is not 0, is also alternatively $NH_2$; $NR^{19}R^{20}$, $N(R^{19}R^{20}R^{21}) \oplus A^\ominus$ or $CONR^5R^6$, where $R^{19}$, $R^{21}$, $R^5$, $R^6$ and $A^\oplus$ are as defined above; hydroxyl; $CO_2H$; or $SO_3H$; or

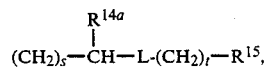

wherein
$R^{15}$ is hydrogen; unsubstituted or monosubstituted $C_1$-$C_{6l}$-alkyl, where the substituent is amino or hydroxyl; mono- or di-$C_1$-$C_4$-alkylamino; guanidino; mono-, di- or tri-$C_1$-$C_4$-alkyl-guanidino; —$N(R^5)_3 \oplus A^\ominus$, where $R^5$ and $A^{63}$ are as defined above; aryl-$C_1$-$C_4$-alkyl, where aryl is as defined above; $C_5$-$C_7$-cycloalkyl-$C_1$-$C_4$-alkyl; $C_1$-$C_5$-alkenyl; or Het, as defined above;

L is a single bond, S, SO, $SO_2$, $NR^7$, or $NR^7$—CO, where $R^7$ is as defined above;

s is 0-to-2; and $R^{14a}$ and t are as defined above; and pharmaceutically-acceptable salts thereof.

When any variable (e.g., aryl, Het, $A^\ominus$, $R^1$, $R^5$, $R^6$, $R^7$, $X^1$, Z, n, etc.) occurs more than one time in any constituent or in formula I, its definition on each ocurrence is independent of its definition every other occurrence.

As used herein, "alkyl" is intended to include both branched- and straight-chain saturated aliphatic hydrocarbon groups having the specified number of carbon atoms (Me is methyl, Et is ethyl); "alkoxy" represents an alkyl group of indicated number of carbon atoms attached through an oxygen bridge; and "$C_3$-$C_7$-cycloalkyl" is intended to include saturated ring groups, such as cyclopropyl, cyclobutyl, cyclopentyl, cyclohexyl (Cyh) and cycloheptyl. "Alkanoyl" is intended to include those alkylcarbonyl groups of specified number of carbon atoms, which are exemplified by formyl, acetyl, propanoyl and butanoyl; "alkenyl" is intended to include hydrocarbon chains of either a straight- or branched-configuration and one unsaturation which may occur at any point along the chain, such as ethenyl, propenyl, butenyl, pentenyl, and the like, and includes E and Z forms, where applicable; and "arylalkyl" represents aryl groups as herein defined which are attached through a straight- or branched-chain alkyl group of specified number of carbon atoms, such as, for example, benzyl, phenethyl, 3,3-diphenylpropyl, 3-indolylmethyl, and the like. "Halo", as used herein, means fluoro, chloro, bromo and iodo, and "counterion" is used to represent a small, single negatively-charged specie, such as chloride, bromide, nitrate, acetate, perchlorate, benzoate, maleate, benzene sulfonate, tartrate, hemitartrate and the like.

As used herein, with exceptions as noted, "aryl" is intended to mean phenyl (Ph) or naphthyl, which is optionally-substituted by from one- to three-members independently selected from the group consisting of amino (Am), mono- or di-$C_1$-$C_4$-alkylamino, amino-$C_1$-$C_4$-alkyl, hydroxy-$C_1$-$C_4$-alkyl, di-$C_1$-$C_4$-alkylamino-$C_1$-$C_4$-alkyl, guanidyl, guanidyl-$C_1$-$C_4$-alkyl, hydroxyl, $C_1$-$C_4$-alkoxy, $CF_3$, halo, CHO, $CO_2H$, $CO_2R^7$, $NR^5R^6$, wherein $R^7$, $R^5$ and $R^6$ are as defined above, or $N(R^5)_3\oplus A^\ominus$, wherein $R^5$ is as defined above and $A^\ominus$ is a counterion, as defined herein. "Aroyl" is intended to include those aryl-carbonyl groups which are exemplified by benzoyl and naphthoyl.

The term "Het", as used herein, represents a 5-, 6-, or 7-membered heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized or in the form of an N-oxide, and including any bicyclic group in which any of the above-defined heterocyclic rings is fused to a benzene ring. In the case of a heterocyclic ring containing one or more nitrogen atoms, the point of attachment may be at one of the nitrogen atoms, or at any carbon atom. Examples of such heterocyclic elements include piperidyl, piperidinyl, piperazinyl, 2-oxopiperazinyl, pyrryl, pyrrolinyl, 4-piperidonyl, pyrrolidinyl, pyrazolyl, pyrazolinyl, pyrazolidinyl, imidazolyl, imidazolinyl, imidazolidinyl, pyridyl (pyr), pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, benzothiazolyl, benzoxazolyl, furyl, thienyl, benzothienyl, thiamorpholinyl, thiamorpholinyl sulfoxide, thiamorpholinyl sulfone, azepinyl, 2-oxazepinyl, 2-oxapyrrolidinyl and 2-oxapiperidinyl. The heterocyclic moiety is further optionally-substituted by from one- to four-members independently selected from the group consisting of hydroxyl, thiol, $C_1$-$C_6$-alkyl, $CF_3$, $C_1$-$C_4$-alkoxy, halo, aryl, aryl-$C_1$-$C_4$-alkyl, amino, mono- or di-$C_1$-$C_4$-alkylamino, amino-$C_1$-$C_4$-alkyl, amino-$C_1$-$C_4$-alkyl, hydroxy-$C_1$-$C_4$-alkyl, $C_1$-$C_4$-dialkylamino-$C_1$-$C_4$-alkyl, guanidyl, guanidyl-$C_1$-$C_4$-alkyl, CHO, $CO_2H$, $CO_2R^7$, $NR^5R^6$, wherein $R^7$, $R^5$ and $R^6$ are as defined above, or $N(R^5)_3\oplus A^\ominus$, wherein $R^5$ is as defined above and $A^\ominus$ is counterion, as defined herein.

The following additional abbreviations have also been used herein:

| Abbreviated Designation | |
|---|---|
| | Amino Acid/Residue |
| ACHPA | (3S,4S)—4-amino-5-cyclohexyl-3 hydroxypentanoic acid |
| Cys | cysteine |
| His | D or L-histidine |
| Ile | L-isoleucine |
| Leu | L-leucine |
| Lys | L-lysine |
| Orn | D- or L-ornithine |
| Phe | L-phenylalanine |
| Pro | proline |
| Trp | L-tryptophan |
| Tyr | L-tyrosine |
| | Protecting Group |
| BOC | t-butyloxycarbonyl |
| BOM | benzyloxymethyl |
| CBZ | benzyloxycarbonyl(carbobenzoxy) |
| DNP | 2,4-dinitrophenyl |
| | Activating Group |
| HBT(HOBt) | 1-hydroxybenzotriazole hydrate |
| | Condensing Agent |
| DCCI (DCC) | dicyclohexylcarbodiimide |
| DPPA | dipenylphosphorylazide |
| | Reagent |
| AMP | 4-aminomethylpyridine |
| (BOC)$_2$O | di-t-butyl dicarbonate |
| DEAD | diethyl azodicarboxylate |
| TFA | trifluoroacetic acid |
| | Solvent |
| AcOH (HOAc) | acetic acid |
| DMF | dimethylformamide |
| EtOAc (E) | ethyl acetate |
| Et$_2$O | ether |

The A and B components in the renin inhibitors of the present invention have asymmetric centers and occur as racemates, racemic mixtures and as individual diastereomers, with all isomeric forms being included in the present invention. In general, the preferred chiral forms of the A and B components are those which correspond to the naturally-occurring L-amino acids. The chiral form of the T component may be that which corresponds to either an L- or D-amino acid.

Preferred renin inhibitors according to the instant invention include those wherein E is

where W is OH and G is Q—CO—T—V or Q—CO—V, wherein Q is CH₂ or

where $R^{13a}$ is isopropyl or isobutyl.

Particularly preferred renin inhibitors according to the instant invention then include:

2-(N-morpholinocarbonyl)methyl-3-phenylpropionyl-His-ACHPA-NH-CH(2-butyl)-CH₂NH-CH₂-CH₂-N(CH₂CH₂)₂O;

2-(N-morpholinocarbonyl)methyl-3-phenylpropionyl-His-ACHPA-NH-CH(2-butyl)-CH₂-NH-CH₂-CH₂N(CH₂CH₂)₂O(CH₃)⊕Cl⊖;

2-benzyl-5,5-dimethyl-4-oxohexanoyl-His-ACHPA-NH-CH(i-butyl)-CH₂N(CH₂CH₂)₂N(CH₃)₂⊕Cl⊖;

N-[2-(t-butylsufonylmethyl)-3-phenylpropionyl]-His-ACHPA-NH-CH(i-butyl)-CH₂-NH-(1-ethyl-4,5-dihydroimidazol-2-yl);

N-[2-(t-butylsufonylmethyl)-3-phenylpropionyl]-His-ACHPA-NH-CH₂-CH(2-butyl)-N(CH₃)₂;

N-[1-(morpholin-4-yl)sufonylmethyl-2-phenethylsulfonyl]-His-ACHPA-NH-CH₂-CH(2-butyl)-N(CH₂CH₃)₃⊕Cl⊖;

N-[1-(morpholin-4-yl)sufonylmethyl-2-phenethylsulfonyl]-His-ACHPA-NH-CH₂-CH(2-butyl)-NH-(4,5-dihydroimidazol-2-yl);

N-[1-(morpholin-4-yl)sufonylmethyl-2-phenethylsulfonyl]-His-ACHPA-NH-CH₂-CH(2-butyl)-NH-(1-ethyl-4,5-dihydroimidazol-2-yl);

N-[1-(morpholin-4-yl)sufonylmethyl-2-phenethylsulfonyl]-His-ACHPA-NH-CH(2-butyl)-CH₂-(2-hydroxymethylpyrrolidin-1-yl);

N-[1-(morpholin-4-yl)sufonylmethyl-2-phenethylsulfonyl]-His-ACHPA-NH-CH(2-butyl)-CH₂-(2-guanidinomethylpyrrolidin-1-yl);

N-[1-(morpholin-4-yl)sufonylmethyl-2-phenethylsulfonyl]-His-ACHPA-NH-CH(2-butyl)-CH₂-(2-hydroxymethyl-1-methylpyrrolidinium-1-yl)⊕Cl⊖;

N-[1-(morpholin-4-yl)sufonylmethyl-2-phenethylsulfonyl]-His-ACHPA-NH-CH(2-butyl)-CH₂-(2-carboxy-1-methylpyrrolidinium-1-yl) inner salt;

N-[1-(thiamorpholin-4-yl-S,S-dioxide)sufonylmethyl-2-phenethylsulfonyl]-His-ACHPA-NH-CH(2-butyl)-CH₂-(2-trimethylammoniomethylpyrrolidin-1-yl)⊕Cl⊖;

N-[1-(thiamorpholin-4-yl-S,S-dioxide)sufonylmethyl-2-phenethylsulfonyl]-His-ACHPA-NH-CH(2-butyl)-CH₂-N(CH₃)₂⊕CH₂CO₂⊖;

N-[1-(thiamorpholin-4-yl-S,S-dioxide)sufonylmethyl-2-phenethylsulfonyl]-His-ACHPA-NH-CH(2-butyl)-CH(OH)-CH₂-N(CH₃)(CH₂CH₂)₂O⊕Cl⊖;

N-[1-(thiamorpholin-4-yl-S,S-dioxide)sufonylmethyl-2-phenethylsulfonyl]-His-ACHPA-NH-CH(2-butyl)-CH₂-(pyridinium-1-yl)⊖Cl⊕;

N-[1-(thiamorpholin-4-yl-S,S-dioxide)sufonylmethyl-2-phenethylsulfonyl]-His-ACHPA-NH-CH(2-butyl)-CH₂-1-methylimidazolium-1-yl)⊕Cl⊖;

N-[1-(thiamorpholin-4-yl-S,S-dioxide)sufonylmethyl-2-phenethylsulfonyl]-His-ACHPA-NH-CH(2-butyl)-CH₂-N(CH₃)₂⊕CH₂CH₂CO₂⊖;

2-(N-morpholinocarbonyl)methyl-3-phenylpropionyl-His-ACHPA-NH-2(S)-methylbutyl;

2-benzyl-5,5-dimethyl-4-oxohexanoyl-His-ACHPA-NH-2(S)-methylbutyl;

N-(benzimidazol-2-yl)sulfonyl-His-ACHPA-NH-2(S)-methylbutyl;

N-(benzimidazol-2-yl)carbonyl-His-ACHPA-NH-2(S)-methylbutyl;

N-(indol-2-yl)carbonyl-His-ACHPA-NH-2(S)-methylbutyl;

N-[2-(t-butylsufonylmethyl)-3-phenylpropionyl]-His-ACHPA-NH-2(S)-methylbutyl;

N-[2-(i-propylsufonylmethyl)-3-phenylpropionyl]-His-ACHPA-NH-2(S)-methylbutyl;

N-[2-(i-propylsufonylmethyl)-3-phenylpropionyl]-Nle-ACHPA-NH-2(S)-methylbutyl;

N-[1-(t-butylsufonylmethyl)-2-phenethylsulfonyl]-His-ACHPA-NH-2(S)-methylbutyl;

N-[1-(imidazol-4-yl)sufonylmethyl-2-phenethylsulfonyl]-His-ACHPA-NH-2(S)-methylbutyl;

N-[1-(1,1,-dimethyl-2-carboxyethyl)sufonylmethyl-2-phenethylsulfonyl]-His-ACHPA-NH-2(S)-methylbutyl;

N-[1-(p-carboxyphenyl)sufonylmethyl-2-phenethylsulfonyl]-His-ACHPA-NH-2(S)-methylbutyl;

N-[1-(p-aminophenyl)sufonylmethyl-2-phenethylsulfonyl]-His-ACHPA-NH-2(S)-methylbutyl;

N-[1-(thiamorpholin-4-yl-S,S-dioxide)sufonylmethyl-2-phenethylsulfonyl]-His-ACHPA-NH-2(S)-methylbutyl;

N-[1-(4-ethylpiperazin-1-yl)sulfonylmethyl)-2-phenethylsulfonyl]-Nle-ACHPA-NH-2(S)-methylbutyl;

N-(N-benzyl-N'-morpholinocarbonylmethyl)carbamoyl-His-ACHPA-NH-2(S)-methylbutyl;

N-(N-benzyl-N'-morpholinocarbonylmethyl)sulfonamido-His-ACHPA-NH-2(S)-methylbutyl;

N-(N-benzyl-N'-thiamorpholinocarbonylmethyl-S,S-dioxide)carbamoyl-His-ACHPA-NH-2(S)-methylbutyl;

N-[1-(N-morpholinocarbonyl)methyl-2-phenethylsulfonyl]-His-ACHPA-NH-2(S)-methylbutyl;

2-(N-morpholinocarbonyl)methyl-3-phenylpropionyl-His-ACHPA-NH-2(S)-methylbutyl dihydrochloride;

2-(N-morpholinocarbonyl)methyl-3-phenylpropionyl-His-ACHPA-NH-CH(2-butyl)-CH₂-NH(CH₂CH₂)₂O;

2-(N-morpholinocarbonyl)methyl-3-phenylpropionyl-His-ACHPA-NH-CH(2-butyl)-CH₂-NH(CH₂CH₂)₂SO₂;

2-(N-morpholinocarbonyl)methyl-3-phenylpropionyl-His-ACHPA-NH-CH(2-butyl)-CH₂-N(CH₂CH₂)₂O(CH₃)⊕ Cl⊖;

2-benzyl-5,5-dimethyl-4-oxohexanoyl-His-ACHPA-NH-CH(2-butyl)-CH₂-NH(CH₂CH₂)₂NCH₃;

2-benzyl-5,5-dimethyl-4-oxohexanoyl-His-ACHPA-NH-CH(2-butyl)-CH₂-N(CH₃)(CH₂CH₂)₂NCH₃⊕ Cl⊖;

2-benzyl-5,5-dimethyl-4-oxohexanoyl-His-ACHPA-NH-CH(2-butyl)-CH₂-N(CH₃)(CH₂CH₂)₂SO₂⊕ Cl⊖;

N-[2-(t-butylsufonylmethyl)-3-phenylpropionyl]-His-ACHPA-NH-CH(2-butyl)-CH₂-NH(CH₂CH₂)₂N(CH₃)₂⊕ Cl⊖;

N-[2-(t-butylsufonylmethyl)-3-phenylpropionyl]-His-ACHPA-NH-CH(2-butyl)-CH₂-NH(CH₂CH₂)₂N-CO-CH₃;

N-[2-(t-butylsufonylmethyl)-3-phenylpropionyl]-His-ACHPA-NH-CH(2-butyl)-CH₂-N(CH₃)₂;

N-[2-(t-butylsufonylmethyl)-3-phenylpropionyl]-His-ACHPA-NH-CH(2-butyl)-CH2-N(CH3)3⊕ Cl⊖;

N-[2-(t-butylsufonylmethyl)-3-phenylpropionyl]-His-ACHPA-N(i-propyl)-CH(2-butyl)-CH2-N(CH3)3⊕ Cl⊖;

N-[1-(morpholin-4-yl)sufonylmethyl-2-phenethylsulfonyl]-His-ACHPA-N(CH3)-CH(2-butyl)-CH2-N(CH3)3⊕ Cl⊖;

N-[1-(morpholin-4-yl)sufonylmethyl-2-phenethylsulfonyl]-His-ACHPA-N(i-butyl)-CH(2-butyl)-CH2-N(CH3)3⊕ Cl⊖;

N-[1-(morpholin-4-yl)sufonylmethyl-2-phenethylsulfonyl]-His-ACHPA-NH-CH(2-butyl)-CH2-N(CH2CH3)3⊕ Cl⊖;

N-[1-(morpholin-4-yl)sufonylmethyl-2-phenethylsulfonyl]-His-ACHPA-NH-CH(2-butyl)-CH2-CH2-NH(CH2CH2)2O;

N-[1-(thiamorpholin-4-yl)sufonylmethyl-2-phenethylsulfonyl]-His-ACHPA-NH-CH(2-butyl)-CH2-CH2-NH(CH2CH2)2SO2;

N-[1-(thiamorpholin-4-yl-S,S-dioxide)sufonylmethyl-2-phenethylsulfonyl]-His-ACHPA-NH-CH(2-butyl)-CH2-CH2-N(CH2CH3)3⊕ Cl⊖;

N-[2-(t-butylsufonylmethyl)-3-phenylpropionyl]-(S-imidazol-4-yl)Cys-ACHPA-NH-CH(2-butyl)-CH2-CH2-CH2-N(CH2CH3)3⊕ Cl⊖;

N-(benzimidazol-2-yl)sulfonyl-His-Cal[CH(OH)CH2]-Val-NH-CH(2-butyl)-CH2-NH-(4,5-dihydroimidazol-2-yl);

N-(benzimidazol-2-yl)sulfonyl-His-Cal[CH(OH)CH2]-Val-NH-CH(2-butyl)-CH2-NH-(1-ethyl-4,5-dihydroimidazol-2-yl);

N-(benzimidazol-2-yl)sulfonyl-His-Cal[CH(OH)CH2]-Val-NH-CH(2-butyl)-CH2-NH-(1-ethyl-pyridinium-4-yl)⊕ Cl⊖;

N-(benzimidazol-2-yl)sulfonyl-His-Cal[CH(OH)CH2]-Val-NH-CH(2-butyl)-CH2-(3-amino-pyrrolidin-1-yl);

N-(benzimidazol-2-yl)sulfonyl-His-Cal[CH(OH)CH2]-Val-NH-CH(2-butyl)-CH2-(1-methyl-3-oxopiperidinium-1-yl)⊕ Cl⊖;

N-[2-(i-propylsufonylmethyl)-3-phenylpropionyl]-His-AmACHPA-NH-CH(2-butyl)-CH2-(3-dimethylaminopiperidin-1-yl);

N-[2-(i-propylsufonylmethyl)-3-phenylpropionyl]-His-AmACHPA-NH-CH(2-butyl)-CH2-(3-trimethylammonium-piperidin-1-yl);

N-[2-(i-propylsufonylmethyl)-3-phenylpropionyl]-His-(2S-i-butyl)ACHPA-NH-CH(2-butyl)-CH2-NH-(1,1-dimethylpiperidinium-4-yl)⊕ Cl⊖;

N-[2-(i-propylsufonylmethyl)-3-phenylpropionyl]-His-(2S-allyl)ACHPA-NH-CH(2-butyl)-CH2-NH-(3,4,5,6-tetrahydropyrazol-2-yl);

N-(benzimidazol-2-yl)sulfonyl-His-Cal[CH(NH2)CH2]-Val-NH-CH(2-butyl)-CH2-NH-(1-methylazepin-3-yl);

N-[2-(t-butylsufonylmethyl)-3-phenylpropionyl]-His-ACHPA-NH-CH(2-butyl)-CH2-NH-(1,1-dimethylazepinium-3-yl)⊕ Cl⊖;

N-[2-(i-propylsufonylmethyl)-3-phenylpropionyl]-His-ACHPA-NH-CH(2-butyl)-CH2-NH-(3-quinuclidinyl);

N-[1-(imidazol-4-yl)sufonylmethyl-2-phenethylsulfonyl]-His-ACHPA-NH-CH(2-butyl)-CH2-NH-(N-methyl-quinuclidinium-3-yl)⊕ Cl⊖;

N-[1-(1,1,-dimethyl-2-carboxyethyl)sufonylmethyl-2-phenethylsulfonyl]-His-ACHPA-NH-CH(2-butyl)-CH2-NH-CH2Ph;

N-[1-(p-carboxyphenyl)sufonylmethyl-2-phenethylsulfonyl]-His-ACHPA-NH-CH(2-butyl)-CH2-N(CH3)-CH2Ph;

N-[1-(thiamorpholin-4-yl-S,S-dioxide)sufonylmethyl-2-phenethylsulfonyl]-His-ACHPA-NH-CH(2-butyl)-CH2-N(CH3)2-CH2Ph⊕ Cl⊖;

N-[1-(4-ethylpiperazin-1-yl)sufonylmethyl)-2-phenethylsulfonyl]-Nle-ACHPA-NH-CH(2-butyl)-CH2-NH-CH2-(4-pyridyl);

N-(N-benzyl-N'-morpholinocarbonylmethyl)carbamoyl-His-ACHPA-NH-CH(2-butyl)-CH2-NH-CH2-(1-methylpyridinium-4-yl)⊕ Cl⊖;

N-[1-(N-morpholinocarbonyl)methyl-2-phenethylsulfonyl]-His-ACHPA-NH-CH(2-butyl)-CH2-NH-CH2-(1-ethylpyrrolidin-3-yl);

N-[1-(morpholin-4-yl)sufonylmethyl-2-phenethylsulfonyl]-His-ACHPA-NH-CH(2-butyl)-CH2-N(CH3)2⊕CH2CH2SO3⊖;

N-[1-(morpholin-4-yl)sufonylmethyl-2-phenethylsulfonyl]-His-ACHPA-NH-CH(2-butyl)-CH2-N(CH3)2⊕CH2CH2OH Cl⊖;

2-(N-morpholinocarbonyl)methyl-3-phenylpropionyl-His-ACHPA-Lys-NHCH2(pyridin-4-yl);

2-benzyl-5,5-dimethyl-4-oxohexanoyl-His-ACHPA-NH-Lys-NHCH2(pyridin-4-yl);

N-(benzimidazol-2-yl)sulfonyl-His-ACHPA-Lys-NH(quinuclidin-3-yl);

N-(benzimidazol-2-yl)carbonyl-His-ACHPA-Lys-NHCH2(pyridin-2-yl);

[N-(indol-2-yl)carbonyl-His-ACHPA-Lys-NHCH(2-butyl)-CH2N(CH3)3]⊕ OAc⊖;

N-[2-(i-propylsufonylmethyl)-3-phenylpropionyl]-His-ACHPA-Lys-NHCH2(pyridin-4-yl);

N-[2-(i-propylsufonylmethyl)-3-phenylpropionyl]-Nle-ACHPA-Lys-NHCH2(pyridin-4-yl);

N-[1-(t-butylsufonylmethyl)-2-phenethylsulfonyl]-His-ACHPA-Ly-NH-2(S)-methylbutyl;

N-[1-(imidazol-4-yl)sufonylmethyl-2-phenethylsulfonyl]-His-ACHPA-(Nε-imidazolin-2-yl)Lys-NH-i-Bu;

N-[1-(1,1,-dimethyl-2-carboxyethyl)sufonylmethyl-2-phenethylsulfonyl]-His-ACHPA-(Nε,Nε-dimethyl)Lys-NHCH2(pyridin-4-yl);

N-[1-(p-carboxyphenyl)sufonylmethyl-2-phenethylsulfonyl]-His-ACHPA-NHCH[(CH2)4NHC(=NCH3)NHCH3]CO-NHCH2Ph;

N-[1-(p-aminophenyl)sufonylmethyl-2-phenethylsulfonyl]-His-ACHPA-(Nα-CH3)Lys-NH-n-butyl;

N-[1-(thiamorpholin-4-yl-S,S-dioxide)sufonylmethyl-2-phenethyl-sulfonyl]-His-ACHPA-(Nε-imidazolin-2-yl)Lys-NH-i-Bu;

N-[1-(4-ethylpiperazin-1-yl)sufonylmethyl)-2-phenethylsulfonyl]-Nle-ACHPA-Lys-NH2;

N-(N-benzyl-N'-morpholinocarbonylmethyl)carbamoyl-His-ACHPA-(Nε-pyridin-4-yl)Lys-NH-2(S)-methylbutyl;

N-(N-benzyl-N'-morpholinocarbonylmethyl)sulfonamido-His-ACHPA-Lys-NHCH2(pyridin-4-yl);

N-(N-benzyl-N'-thiamorpholinocarbonylmethyl-S,S-dioxide)-carbamoyl-His-ACHPA-Lys-NH-2(S)-methylbutyl;

N-[1-(N-morpholinocarbonyl)methyl-2-phenethylsulfonyl]-His-ACHPA-Lys-NHCH2(pyridin-3-yl);

[2-(N-morpholinocarbonyl)methyl-3-phenylpropionyl-His-ACHPA-HLys-NHCH2CH2N(CH3)3]⊕ Cl⊖;

2-(N-morpholinocarbonyl)methyl-3-phenylpropionyl-His-ACHPA-NHCH(CH$_2$CH$_2$NHPh)CONHCH$_2$-(pyridin-4-yl);

2-(N-morpholinocarbonyl)methyl-3-phenylpropionyl-His-ACHPA-(N$^\alpha$-CH$_3$)Lys-NHCH$_2$(pyridin-4-yl);

2-(N-morpholinocarbonyl)methyl-3-phenylpropionyl-His-ACHPA-Lys-NHCH$_2$(pyridin-4-yl);

2-benzyl-5,5-dimethyl-4-oxohexanoyl-His-ACHPA-Lys-NHCH$_2$(piperidin-4-yl);

2-benzyl-5,5-dimethyl-4-oxohexanoyl-His-ACHPA-Lys-NHCH$_2$(pyridin-4-yl);

[2-benzyl-5,5-dimethyl-4-oxohexanoyl-His-ACHPA-Lys-NH-[(N-(CH$_3$)-quinuclidin-3-yl)]]$^\oplus$ Cl$^\ominus$;

N-[2-(t-butylsufonylmethyl)-3-phenylpropionyl]-His-ACHPA-Lys-NH-CH(2-butyl)CH$_2$N(CH$_3$)$_2$;

N-[2-(t-butylsufonylmethyl)-3-phenylpropionyl]-His-ACHPA-Lys-NH-CH(2-butyl)CH$_2$N(CH$_2$CH$_2$)$_2$O;

N-[2-(t-butylsufonylmethyl)-3-phenylpropionyl]-His-ACHPA-(N$^\alpha$-CH$_3$)Lys-NHCH$_2$(piperidin-4-yl);

N-[2-(t-butylsufonylmethyl)-3-phenylpropionyl]-His-ACHPA-Lys-N(CH$_3$)CH$_2$(piperidin-4-yl);

N-[2-(t-butylsufonylmethyl)-3-phenylpropionyl]-His-ACHPA-Lys-N(CH$_3$)CH$_2$(1-methylpiperidin-4-yl);

N-[1-(morpholin-4-yl)sufonylmethyl-2-phenethylsulfonyl]-His-ACHPA-(N$^\alpha$-CH$_3$)Lys-N(CH$_3$)(piperidin-4-yl);

N-[1-(morpholin-4-yl)sufonylmethyl-2-phenethylsulfonyl]-His-ACHPA-(N$^\alpha$-CH$_3$)Lys-N(CH$_3$)(1-ethylpiperidin-4-yl);

N-[1-(morpholin-4-yl)sufonylmethyl-2-phenethylsulfonyl]-His-ACHPA-(N$^\alpha$-CH$_3$)Lys-NH(pyridin-4-yl);

N-[1-(thiamorpholin-4-yl)sufonylmethyl-2-phenethylsulfonyl]-His-ACHPA-(N$^\alpha$-CH$_3$)Lys-NH(pyridin-4-yl);

N-[1-(thiamorpholin-4-yl-S,S-dioxide)sufonylmethyl-2-phenethylsulfonyl]-His-ACHPA-Lys-NH-2(S)-methylbutyl;

N-[2-(t-butylsufonylmethyl)-3-phenylpropionyl]-(S-imidazol-4-yl)Cys-ACHPA-Lys-N(CH$_3$)(pyridin-3-yl);

N-(benzimidazol-2-yl)sulfonyl-His-Cal[CH(OH)CH$_2$]-Val-Lys-NH-2(S)-methylbutyl;

N-(benzimidazol-2-yl)sulfonyl-His-Cal[CH(OH)CH$_2$]-Val-Lys-NHCH$_2$(pyridin-4-yl);

N-(benzimidazol-2-yl)sulfonyl-His-Cal[CH(OH)CH$_2$]-Val-(N$^\epsilon$-CH$_3$)Lys-N(CH$_3$)(1-ethylpiperidin-4-yl);

N-(benzimidazol-2-yl)sulfonyl-His-Cal[CH(OH)CH$_2$]-Val-Lys-NH-n-butyl;

N-(benzimidazol-2-yl)sulfonyl-His-Cal[CH(OH)CH$_2$]-Val-(N$^\epsilon$-CH$_3$)Lys-NH(pyridin-4-yl);

N-[2-(i-propylsufonylmethyl)-3-phenylpropionyl]-His-AmACHPA-Lys;

N-[2-(i-propylsufonylmethyl)-3-phenylpropionyl]-His-AmACHPA-Lys-N(CH$_3$)(1-ethylpiperidin-4-yl);

N-[2-(i-propylsufonylmethyl)-3-phenylpropionyl]-His-(2S-i-butyl)ACHPA-Lys-NHCH$_3$;

N-[2-(i-propylsufonylmethyl)-3-phenylpropionyl]-His-(2S-allyl)ACHPA-(N-CH$_3$)Lys-NHCH$_2$(pyridin-4-yl);

N-(benzimidazol-2-yl)sulfonyl-His-Cal[CH(NH$_2$)CH$_2$]-Val-Lys;

[N-[2-(t-butylsufonylmethyl)-3-phenylpropionyl]-His-ACHPA-Lys-NH-CH(2-butyl)-CH$_2$-NH-(1,1-dimethylazepinium-3-yl)]$^\oplus$ Cl$^\ominus$;

N-[2-(i-propylsufonylmethyl)-3-phenylpropionyl]-His-ACHPA-(N-CH$_3$)Orn-NHCH$_2$CH$_2$N(CH$_2$CH$_2$)$_2$O;

N-[(2-butyl-5-(morpholinocarbonyl)methyl-6-phenyl-4-thiahexanoyl-S,S-dioxide)]-ACHPA-NH-2(S)-methylbutyl;

N-[(2-(imidazol-4-yl)methyl-5-(morpholinocarbonyl)-methyl-6-phenyl-4-thiahexanoyl S,S-dioxide)]-ACHPA-NH-2(S)-methylbutyl;

N-[(2S-butyl-5-(thiamorpholinocarbonyl-S,S-dioxide)-methyl-6-phenyl-4-thiahexanoyl)]-ACHPA-NH-2(S)-methylbutyl;

N-[(1S-butyl-4-(morpholinocarbonyl)methyl-5-phenyl-3-thiapentanesulfonyl-S,S-dioxide)]-ACHPA-NH-2(S)-methylbutyl;

N-[(1S-butyl-4-(thiamorpholinocarbonyl-S,S-dioxide)-methyl-5-phenyl-3-thiapentanesulfonyl-S,S-dioxide)]-His-ACHPA-NH-2(S)-methylbutyl;

N-[2-(benzimidazol-2-yl)sulfonyl)methylhexanoyl]-ACHPA-NH-CH(2-butyl)-CH$_2$-NH(CH$_2$CH$_2$)$_2$O;

N-[2-(indol-2-yl)sulfonyl)methylhexanoyl]-ACHPA-NH-CH(2-butyl)-CH$_2$-NH(CH$_2$CH$_2$)$_2$SO$_2$;

N-[2-(benzimidazol-2-yl)carbonyl)methylhexanoyl]-ACHPA-NH-CH(2-butyl)-CH$_2$-N(CH$_2$CH$_2$)$_2$O(CH$_3$)$^\oplus$ Cl$^\ominus$;

N-[2-(indol-2-yl)carbonyl)methylhexanoyl]-ACHPA-NH-CH(2-butyl)-CH$_2$-NH(CH$_2$CH$_2$)$_2$NCH$_3$;

N-[2-butyl-5-(N-morpholinocarbonyl)amino-4-oxohexanoyl]-ACHPA-NH-CH(2-butyl)-CH$_2$-N(CH$_3$)(CH$_2$CH$_2$)$_2$-NCH$_3$$^\oplus$ Cl$^\ominus$;

N-[5-(N-morpholinocarbonyl)amino-4-oxo-2-phenylthiomethyl-hexanoyl]-ACHPA-NH-CH(2-butyl)-CH$_2$-N(CH$_3$)(CH$_2$CH$_2$)$_2$-NCH$_3$$^\oplus$ Cl$^\ominus$;

N-[2-(imidazol-4-yl)methyl-5-(N-morpholinocarbonyl)amino-4-oxohexanoyl]-ACHPA-NH-CH(2-butyl)-CH$_2$-N(CH$_3$)-(CH$_2$CH$_2$)$_2$SO$_2$$^\oplus$ Cl$^\ominus$;

N-[2-(S-imidazol-4-yl)thiomethyl-5-(N-morpholinocarbonyl)amino-4-oxohexanoyl]-ACHPA-NH-CH(2-butyl)-CH$_2$-N(CH$_3$)-(CH$_2$CH$_2$)$_2$SO$_2$$^\oplus$ Cl$^\ominus$;

N-[5-(t-butylsulfonyl)methyl-2-(imidazol-4-yl)methyl-4-oxo-6-phenylhexanoyl]-ACHPA-NH-CH(2-butyl)-CH$_2$-NH(CH$_2$CH$_2$)$_2$N(CH$_3$)$_2$$^\oplus$ Cl$^\ominus$;

N-[5-(morpholinosulfonyl)methyl-2-(imidazol-4-yl)methyl-4-oxo-6-phenylhexanoyl]-ACHPA-NH-CH(2-butyl)-CH$_2$-NH(CH$_2$CH$_2$)$_2$N(CH$_3$)$_2$$^\oplus$ Cl$^\ominus$;

N-[2-n-butyl-5-(t-butylsulfonyl)methyl-4-oxo-6-phenylhexanoyl]-ACHPA-NH-CH(2-butyl)-CH$_2$-NH(CH$_2$CH$_2$)$_2$N-CO-CH$_3$;

N-[2-(N-benzyl-N'-(morpholinocarbonyl)methyl)sulfonamidomethyl)hexanoyl]-ACHPA-NH-CH(2-butyl)-CH$_2$-N(CH$_3$)$_2$;

N-[2-n-butyl-5-(t-butylsulfonyl)methyl-4-hydroxy-6-phenylhexanoyl]-ACHPA-NH-CH(2-butyl)-CH$_2$-N(CH$_3$)$_3$$^\oplus$ Cl$^\ominus$;

N-[5-(t-butylsulfonyl)methyl-2-(imidazol-4-yl)methyl-4-oxo-6-phenylhexanoyl]-ACHPA-NH-CH$_2$-CH(2-butyl)-N(CH$_2$CH$_3$)$_3$$^\oplus$ Cl$^\ominus$;

N-[5-(t-butylsulfonyl)methyl-2-(imidazol-4-yl)methyl-4-oxo-6-phenylhexanoyl]-ACHPA-NH-CH$_2$-CH(2-butyl)-NH-(4,5-dihydroimidazol-2-yl);

N-[5-(t-butylsulfonyl)methyl-2-(imidazol-4-yl)methyl-4-oxo-6-phenylhexanoyl]-ACHPA-NH-CH$_2$-CH(2-butyl)-NH-(1-ethyl-4,5-dihydroimidazol-2-yl);

N-[5-(t-butylsulfonyl)methyl-2-(imidazol-4-yl)methyl-4-oxo-6-phenylhexanoyl]-ACHPA-NH-CH(2-butyl)-CH$_2$-(2-hydroxymethylpyrrolidin-1-yl);

N-[5-(t-butylsulfonyl)methyl-2-(imidazol-4-yl)methyl-4-oxo-6-phenylhexanoyl]-ACHPA-NH-CH(2-butyl)-CH$_2$-(2-guanidinomethylpyrrolidin-1-yl);

N-[5-(t-butylsulfonyl)methyl-2-(imidazol-4-yl)methyl-4-oxo-6-phenylhexanoyl]-ACHPA-NH-CH(2-butyl)-

CH$_2$-(2-hydroxymethyl-1-methylpyrrolidinium-1-yl)$^\oplus$ Cl$^\ominus$;

N-[5-(morpholinosulfonyl)methyl-2-(imidazol-4-yl)methyl-4-oxo-6-phenylhexanoyl]-ACHPA-NH-CH(2-butyl)-CH$_2$-NH(CH$_2$CH$_2$)$_2$N(CH$_3$)$_2$$^\oplus$ Cl$^\ominus$;

N-[5-(morpholinosulfonyl)methyl-2-(imidazol-4-yl)methyl-4-oxo-6-phenylhexanoyl]-ACHPA-NH-CH(2-butyl)-CH$_2$-NH(CH$_2$CH$_2$)$_2$N(CH$_3$)$_2$$^\oplus$ Cl$^\ominus$;

N-[5-(morpholinosulfonyl)methyl-2-(imidazol-4-yl)methyl-4-oxo-6-phenylhexanoyl]-ACHPA-NH-CH(2-butyl)-CH$_2$-NH(CH$_2$CH$_2$)$_2$N(CH$_3$)$_2$$^\oplus$ Cl$^\ominus$;

N-[5-(morpholinosulfonyl)methyl-2-(imidazol-4-yl)methyl-4-oxo-6-phenylhexanoyl]-ACHPA-NH-CH(2-butyl)-CH$_2$-NH(CH$_2$CH$_2$)$_2$N(CH$_3$)$_2$$^\oplus$ Cl$^\ominus$;

N-[5-(morpholinosulfonyl)methyl-2-(imidazol-4-yl)methyl-4-oxo-6-phenylhexanoyl]-ACHPA-NH-CH(2-butyl)-CH$_2$-NH(CH$_2$CH$_2$)$_2$N(CH$_3$)$_2$$^\oplus$ Cl$^\ominus$;

N-[5-(morpholinosulfonyl)methyl-2-(imidazol-4-yl)methyl-4-oxo-6-phenylhexanoyl]-ACHPA-NH-CH(2-butyl)-CH$_2$-NH(CH$_2$CH$_2$)$_2$N(CH$_3$)$_2$$^\oplus$ Cl$^\ominus$;

N-[5-(morpholinosulfonyl)methyl-2-(imidazol-4-yl)methyl-4-oxo-6-phenylhexanoyl]-ACHPA-NH-CH(2-butyl)-CH$_2$-NH(CH$_2$CH$_2$)$_2$N(CH$_3$)$_2$$^\oplus$ Cl$^\ominus$;

N-[(2S-butyl-5-(morpholinocarbonyl)methyl-6-phenyl-4-thiahexanoyl-S,S-dioxide)]-ACHPA-NH-CH(2-butyl)-CH$_2$-(2-trimethylammoniomethylpyrrolidin-1-yl)$^\oplus$ Cl$^\ominus$;

N-[(2S-butyl-5-(morpholinocarbonyl)methyl-6-phenyl-6-phenyl-4-thiahexanoyl S,S-dioxide)];

N-[(2S-butyl-5-(morpholinocarbonyl)methyl-6-phenyl-4-thiahexanoyl-S,S-dioxide)]-ACHPA-MH-CH(2-butyl)-CH$_2$-N(CH$_3$)$_2$$^\oplus$CH$_2$CO$_2$$^\ominus$;

N-[(2S-butyl-5-(morpholinocarbonyl)methyl-6-phenyl-4-thiahexanoyl-S,S-dioxide)]-ACHPA-NH-CH(2-butyl)-CH(OH)-CH$_2$-N(CH$_3$)(CH$_2$CH$_2$)$_2$O$^\oplus$ Cl$^\ominus$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-CH$_2$-(pyridinium-1-yl)$^\oplus$Cl$^\ominus$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-CH$_2$-1-methylimidazoliuml-yl)$^\oplus$ Cl$^\ominus$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-CH$_2$-N(CH$_3$)$_2$$^\oplus$CH$_2$CH$_2$CO$_2$$^\ominus$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-CH$_2$-N(CH$_3$)$_2$$^\oplus$CH$_2$CH$_2$SO$_3$$^\ominus$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-CH$_2$-N(CH$_3$)$_2$$^\oplus$CH$_2$CH$_2$OH Cl$^\ominus$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-CH$_2$-N(CH$_3$)$_2$$^\oplus$CH$_2$CH$_2$N(CH$_3$)$_2$ Cl$^\ominus$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-CH$_2$-NH-CH$_2$CH$_2$NH-C(=NH)-NH$_2$;

N-[(2-(imidazol-4-yl)methyl-5-(morpholinocarbonyl)methyl-6-phenyl-4-thiahexanoyl-S,S-dioxide)]-Cal[CH(OH)CH$_2$]-Val-NH-CH(2-butyl)-CH$_2$-NH-CH$_2$CH(NH$_2$)CO$_2$H;

N-[(2-(imidazol-4-yl)methyl-5-(morpholinocarbonyl)methyl-6-phenyl-4-thiahexanoyl-S,S-dioxide)]-AmACHPA-NH-CH(2-butyl)-CH$_2$-NH-CH$_2$CH(CO$_2$$^\ominus$)N(CH$_3$)$_3$$^\oplus$;

N-[(2-(imidazol-4-yl)methyl-5-(morpholinocarbonyl)methyl-6-phenyl-4-thiahexanoyl-S,S-dioxide)]-Cal[CH(OH)CH$_2$]Val-N(i-butyl)-CH$_2$-CH$_2$-N(CH$_2$CH$_2$)$_2$N(CH$_3$)$_2$$^\oplus$ Cl$^\ominus$;

N-[(2-(imidazol-4-yl)methyl-5-(morpholinocarbonyl)methyl-6-phenyl-4-thiahexanoyl-S,S-dioxide)]-(2S-i-butyl)-ACHPA-NH-CH(2butyl)-CH$_2$-NH-CH$_2$(pyridin-4-yl N-oxide);

N-[(2-(imidazol-4-yl)methyl-5-(morpholinocarbonyl)methyl-6-phenyl-4-thiahexanoyl-S,S-dioxide)]-(2S-allyl)ACHPA-NH-CH(2-butyl)-CH$_2$-NH-CH$_2$(pyridin-2-yl N-oxide);

N-[(2-(imidazol-4-yl)methyl-5-(morpholinocarbonyl)methyl-6-phenyl-4-thiahexanoyl-S,S-dioxide)]-Cal[CH(NH$_2$)CH$_2$]-Val-NH-CH(2-butyl)-CH$_2$-NH-CH$_2$(pyridin-2-yl-N-oxide);

N-[(2-butyl-5-(morpholinocarbonyl)methyl-6-phenyl-4-thiahexanoyl-S,S-dioxide)]-Cal(CH(OH)CH$_2$)Val-NH-2(S)-methylbutyl;

N-[(2S-butyl-5-(thiamorpholinocarbonyl-S,S-dioxide)methyl-6-phenyl-4-thiahexanoyl)]-ACHPA-Lys-NH(quinuclidin-3-yl);

N-[(1S-butyl-4-(morpholinocarbonyl)methyl-5-phenyl-3-thiapentanesulfonyl-S,S-dioxide)]-ACHPA-Lys-NHCH$_2$-pyridin-2-yl);

N-[(1S-butyl-4-(thiamorpholinocarbonyl-S,S-dioxide)methyl-5-phenyl-3-thiapentanesulfonyl-S,S-dioxide)]-ACHPA-Lys-NHCH(2-butyl)CH$_2$N(CH$_3$)$_3$]$^\oplus$ OAc$^\ominus$;

[N-[(2-(imidazol-4-yl)methyl-5-(morpholinocarbonyl)methyl-6-phenyl-4-thiahexanoyl-S,S-dioxide)]-ACHPA-Lys-NH$_2$;

[N-[(2-(imidazol-4-yl)methyl-5-(morpholinocarbonyl)methyl-6-phenyl-4-thiahexanoyl-S,S-dioxide)]-ACHPA-Lys-N(CH$_3$)CH$_2$(pyridin-4-yl);

[N-[(2-(imidazol-4-yl)methyl-5-(morpholinocarbonyl)methyl-6-phenyl-4-thiahexanoyl-S,S-dioxide)]-ACHPA-Lys-NHCH$_2$(pyridin-4-yl);

[N-[(2-(imidazol-4-yl)methyl-5-(morpholinocarbonyl)methyl-6-phenyl-4-thiahexanoyl-S,S-dioxide)]-ACHPA-Lys-NH-2(S)-methylbutyl;

N-[5-(morpholinosulfonyl)methyl-2-(imidazol-4-yl)methyl-4-oxo-6-phenylhexanoyl]-ACHPA-(N$^\epsilon$-imidazolin-2-yl)Lys-NH-i-Bu;

N-[5-(morpholinosulfonyl)methyl-2-(imidazol-4-yl)methyl-4-oxo-6-phenylhexanoyl]-ACHPA-(N$^\epsilon$,N$^\epsilon$-dimethyl)-Lys-NHCH$_2$(pyridin-4-yl);

N-[2-n-butyl-5-(t-butylsulfonyl)methyl-4-hydroxy-6-phenylhexanoyl]-ACHPA-NHCH[(CH$_2$)$_4$NHC(=NCH$_3$)-NHCH$_3$]CO-NHCH$_2$Ph;

N-[5-(t-butylsulfonyl)methyl-2-(imidazol-4-yl)methyl-4-oxo-6-phenylhexanoyl]-ACHPA-(N$^\alpha$-CH$_3$)Lys-NH-n-butyl;

N-[5-(morpholinosulfonyl)methyl-2-(imidazol-4-yl)methyl-4-oxo-6-phenylhexanoyl]-ACHPA-(N$^\epsilon$-imidazolin-2-yl)Lys-NH-i-Bu;

N-[5-(morpholinosulfonyl)methyl-2-(imidazol-4-yl)methyl-4-oxo-6-phenylhexanoyl]-ACHPA-Lys-NH$_2$;

N-[(2S-butyl-5-(morpholinocarbonyl)methyl-6-phenyl-4-thiahexanoyl-S,S-dioxide)]-ACHPA-(N$^\epsilon$-pyridin-4-yl)Lys-NH-2(S)-methylbutyl;

N-[(2S-butyl-5-(morpholinocarbonyl)methyl-6-phenyl-4-thiahexanoyl-S,S-dioxide)]-ACHPA-Lys-NHCH$_2$(pyridin-4-yl);

N-[(2S-butyl-5-(morpholinocarbonyl)methyl-6-phenyl-4-thiahexanoyl-S,S-dioxide)]-ACHPA-Lys-NH-2(S)-methylbutyl;

N-[(2S-butyl-5-(morpholinocarbonyl)methyl-6-phenyl-4-thiahexanoyl-S,S-dioxide)]-ACHPA-Lys-NHCH$_2$(pyridin-3-yl);

[N-[(2-(imidazol-4-yl)methyl-5-(morpholinocarbonyl)methyl-6-phenyl-4-thiahexanoyl-S,S-dioxide)]-ACHPA-HLys-NHCH$_2$CH$_2$N(CH$_3$)$_3$]$^\oplus$ Cl$^\ominus$;

N-[(2-(imidazol-4-yl)methyl-5-(morpholinocarbonyl)methyl-6-phenyl-4-thiahexanoyl-S,S-dioxide)]-ACHPA-NHCH(CH$_2$CH$_2$NHPh)CONHCH$_2$(pyridin-4-yl);

N-[2-(N-benzyl-N'-(morpholinocarbonyl)methyl)sulfonamidomethyl)hexanoyl]-ACHPA-(N$^\alpha$-CH$_3$)Lys-NHCH$_2$(pyridin-4-yl);

N-[2-(S-imidazol-4-yl)thiomethyl-5-(N-morpholinocarbonyl)amino-4-oxohexanoyl]-ACHPA-Lys-NHCH$_2$(pyridin-4-yl);

N-[2-(S-imidazol-4-yl)thiomethyl-5-(N-morpholinocarbonyl)amino-4-oxohexanoyl]-ACHPA-Lys-NHCH$_2$(piperidin-4-yl);

N-[2-butyl-5-(N-morpholinocarbonyl)amino-4-oxohexanoyl]-ACHPA-Lys-NHCH$_2$(pyridin-4-yl);

N-[2-butyl-5-(N-morpholinocarbonyl)amino-4-oxohexanoyl]-ACHPA-Lys-(N-CH$_3$-quinuclidin-3-yl)]$^\oplus$ Cl$^\ominus$;

N-[5-(N-morpholinocarbonyl)amino-4-oxo-2-phenylthiomethylhexanoyl]-ACHPA-Lys-NH-CH(2-butyl)CH$_2$N(CH$_3$)$_2$;

N-[5-(N-morpholinocarbonyl)amino-4-oxo-2-phenylthiomethylhexanoyl]-ACHPA-Lys-NH-CH(2-butyl)CH$_2$N(CH$_2$CH$_2$)$_2$O;

N-[5-(N-morpholinocarbonyl)amino-4-oxo-2-phenylthiomethylhexanoyl]-ACHPA-(N$^\alpha$-CH$_3$)Lys-NHCH$_2$(piperidin-4-yl);

N-[4-hydroxy-5-(N-morpholinocarbonyl)amino-2-phenylthiomethylhexanoyl]-ACHPA-Lys-N(CH$_3$)CH$_2$(piperidin-4-yl);

N-[5-(morpholinosulfonyl)methyl-2-(imidazol-4-yl)methyl-4-oxo-6-phenylhexanoyl]-ACHPA-Lys-N(CH$_3$)CH$_2$(1-methylpiperidin-4-yl);

[N-[(2-(imidazol-4-yl)methyl-5-(morpholinocarbonyl)methyl-6-phenyl-4-thiahexanoyl-S,S-dioxide)]-ACHPA-(N$^\alpha$-CH$_3$)-Lys-N(CH$_3$)(piperidin-4-yl);

[N-[(2-(imidazol-4-yl)methyl-5-(morpholinocarbonyl)metyl-6-phenyl-4-thiahexanoyl-S,S-dioxide)]-ACHPA-(N$^\alpha$-CH$_3$)Lys-N(CH$_3$)(1-ethylpiperidin-4-yl);

[N-[(2-(imidazol-4-yl)methyl-5-(morpholinocarbonyl)methyl-6-phenyl-4-thiahexanoyl-S,S-dioxide)]-ACHPA-Lys-NH-2(S)-methylbutyl;

[N-[(2-(imidazol-4-yl)methyl-5-(morpholinocarbonyl)methyl-6-phenyl-4-thiahexanoyl-S,S-dioxide)]-ACHPA-Lys-N(CH$_3$)(pyridin-3-yl);

N-[2-(indol-2-yl)carbonyl)methylhexanoyl]-Cal[CH(OH)-CH$_2$]Val-Lys-NH-2(S)-methylbutyl;

N-[2-(indol-2-yl)carbonyl)methylhexanoyl]-Cal[CH(OH)-CH$_2$]Val-Lys-NHCH$_2$(pyridin-4-yl);

N-[2-(benzimidazol-2-yl)sulfonyl)methylhexanoyl]-Cal[CH(OH)CH$_2$]Val-(N$^\alpha$-CH$_3$)Lys-N(CH$_3$)(1-ethylpiperidin-4-yl);

N-[2-(benzimidazol-2-yl)sulfonyl)methylhexanoyl]-Cal[CH(OH)CH$_2$]Val-Lys-NH-n-butyl;

N-[(2-(imidazol-4-yl)methyl-5-(morpholinocarbonyl)methyl-6-phenyl-4-thiahexanoyl-S,S-dioxide)]-Cal[CH(OH)CH$_2$]Val-(N$^\alpha$-CH$_3$)Lys-NH(pyridin-4-yl);

N-[(2-butyl-5-(morpholinocarbonyl)methyl-6-phenyl-4-thiahexanoyl-S,S-dioxide)]-AmACHPA-Lys;

N-[5-(t-butylsulfonyl)methyl-2-(imidazol-4-yl)methyl-4-oxo-6-phenylhexanoyl]-AmACHPA-Lys-N(CH$_3$)(1-ethylpiperidin-4-yl);

N-[2-(indol-2-yl)sulfonyl)methylhexanoyl]-(2S-i-butyl)-ACHPA-Lys-NHCH$_3$;

N-[2-(benzimidazol-2-yl)carbonyl)methylhexanoyl]-Cal[CH(NH$_2$)CH$_2$]Val-Lys;

N-[2-(benzimidazol-2-yl)carbonyl)methylhexanoyl]-ACHPA-Lys-NH-CH(2-butyl)-CH$_2$NH-(1,1-dimethylazepinium-3-yl)]$^\oplus$ Cl$^\ominus$;

N-[5-(t-butylsulfonyl)methyl-2-(imidazol-4-yl)methyl-4-oxo-6-phenylhexanoyl]-ACHPA-(N$^\alpha$-CH$_3$)Orn-NHCH$_2$CH$_2$N-(CH$_2$CH$_2$)$_2$O;

N[(1-ethoxycarbonylmethyl-2-phenyl)ethylsulfonyl]-His-ACHPA-NH-2(S)-methylbutyl;

N[(1-ethoxycarbonylmethyl-2-phenyl)ethylsulfonyl]-His-ACHPA-Lys-NHCH$_2$(pyridin-4-yl);

N[(1-ethoxycarbonylmethyl-2-phenyl)ethylsulfonyl]-His-ACHPA-Lys-NHCH$_2$(piperidin-4-yl) and N[(1-ethoxycarbonylmethyl-2-phenyl)ethylsulfonyl]-His-ACHPA-Lys-NHiBu.

Pharmaceutically-acceptable salts of the Formula I compounds include acid addition salts, such as: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. The base salts also include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained. Conventional methods of preparing these salts may be used.

There is further provided in the present invention a pharmaceutical composition for treating hypertension and congestive heart failure, comprising a pharmaceutical carrier and a therapeutically-effective amount of a peptide of the formula I. The amount of active ingredient that may be combined with the carrier materials to produce a single dosage form will vary depending upon the host treated and the particular mode of administration.

Also, in accordance with the present invention there is still further provided a method of treating hypertension and congestive heart failure, comprising administering to a patient in need of such treatment, a therapeutically-effective amount of a peptide of the formula I.

The renin inhibitory peptides of the present invention may also be utilized in diagnostic methods for the purpose of establishing the significance of renin as a causative or contributory factor in hypertension or congestive heart failure in a particular patient. For this purpose the present peptides may be administered in a single dose of from 0.1 to 10 mg per kg of body weight.

Both in vivo and in vitro methods may be employed. In the in vivo method, a novel peptide of the present invention is administered to a patient, preferably by intravenous injection, although other routes of parenteral administration are also suitable, at a hypotensive dosage level and as a single dose, and there may result a transitory fall in blood pressure. This fall in blood pressure, if it occurs, indicates supranormal plasma renin levels.

The peptide bond mimic, the statine or other peptide bond isostere which is element R, is prepared by the known methods as follows:

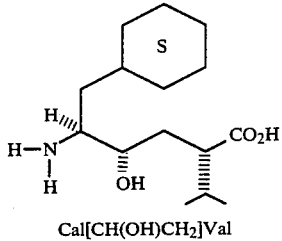

Cal[CH(OH)CH₂]Val

Buhlmayer et al, Homo ACHPA structure, European Pat. Appln. No. 184, 550-A2;

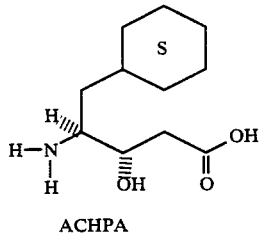

ACHPA

Boger et al., *J. Med. Chem.*, 1985, 28, 1779–1790;

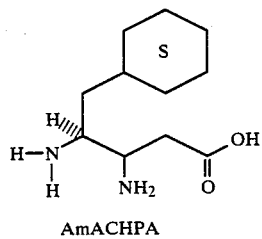

AmACHPA

Raddatz et al., European Pat. Appl. No. 161,588; Szelke et al, PCT Int. Appl. WO 84 03,044;

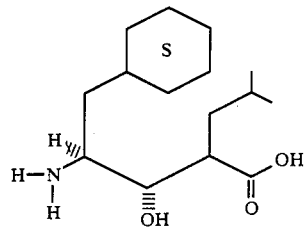

2-Substituted ACHPA

Boger, et al, EP-A 157 409; Veber et al, *Biochem. Soc. Trans*, 1984, 12, 956–959; Stein et al, *Fred. Proc.*, 1986, 45, 869; and

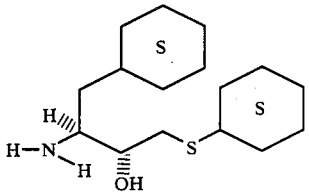

Plattner et al, European Pat. Appl. No. 172,347.

The peptide coupling procedures used in the routes described below include those brought about by use of dicyclohexylcarbodiimide [DCC/hydroxybenzotriazole(HOBt) and of other well-known coupling reagents (Takeda et al, *Tetrahedron Lett*, 1983, 24, 4451–54)].

When the unit T consists of an N-alkyl (for example, N-methyl) amino acid, procedures well-known in peptide synthesis are used to prepare this amino acid and to couple it. In general, the mixed anhydride procedure (with pivaloyl chloride and N-methylmorpholine) is used, as illustrated by Wenger, *Helv. Chem. Acta.*, 1984, 67, 502–525, or the BOP-Cl procedure of Rich et al, *J. Amer. Chem. Soc.*, 1985, 107, 4342–43, is used. N-methyl amino acids may be prepared, for example, by the method of O'Donnell, *Tetrahedron Lett.*, 1984, 25, 3651, while N-alkyl amino acids generally may be prepared by the procedure of Freidinger, *J. Org. Chem.*, 1983, 48, 77–81 or of Hansen et al, *J. Org. Chem.*, 1985, 50, 945–950. N-substituted histidines may be prepared by the procedure of Stillwell, *Bioorganic Chem.*, 1975, 4, 317–325. 945–950. N-substituted histidines may be prepared by the procedure of Stillwell, *Bioorganic Chem.*, 1975, 4, 317–325.

The following schemes outline representative examples of the preparation of peptides of formula I, with similar peptides possessing alternative substituents being prepared by the routes outlined, with necessary modifications within the capabilities of those skilled in the art.

When the A component of the inhibitors of the present invention is a carboxylic acid, for example, of Formula II, preparation of component A may be carried out by either of two routes:

Method 1

Condensation of an aldehyde with diethyl succinate under basic conditions yields an alkylidene succinic acid monoester. Condensation with an amine, for example, with morpholine, provides the corresponding amido ester, which, after hydrogenation and then saponification, provides II.

Method 2

Alkylation of a diethyl alkyl malonate (prepared by alkylation of diethyl malonate) with a chloroamide, for example, with chloroacetylmorpholine amide, provides an amido diester. Hydrolysis and decarboxylation of this amido diester then provides II.

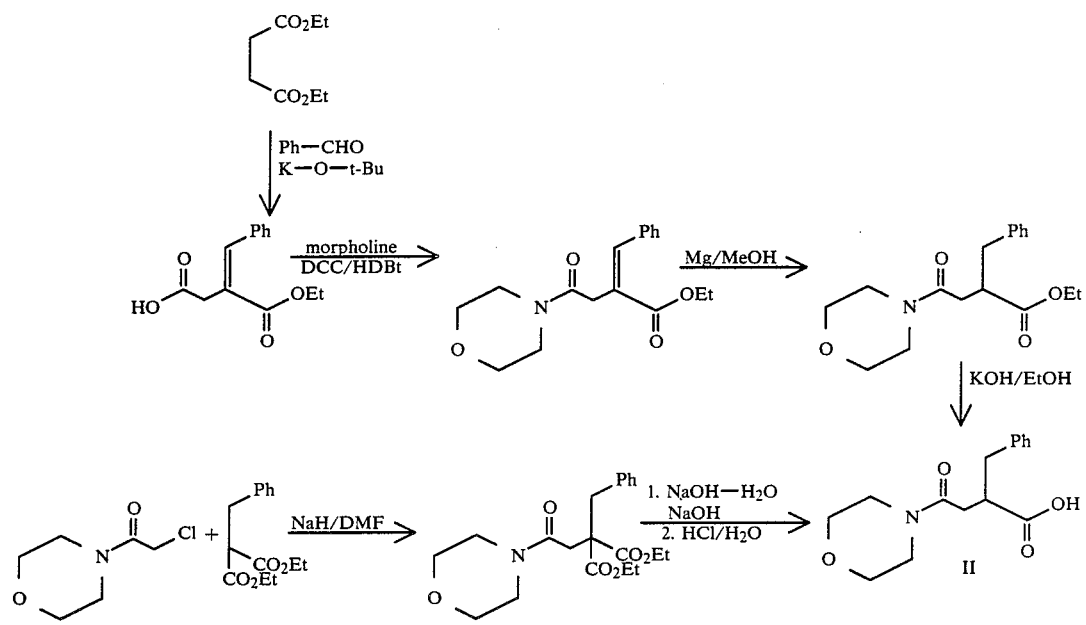

The inhibitors of the present invention may, for example, contain an element A of formula IV, which is prepared according to the following schemes:

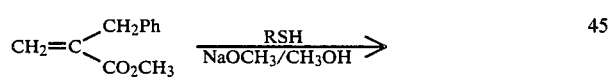

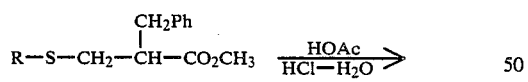

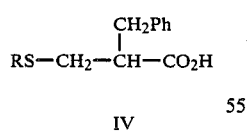

IV

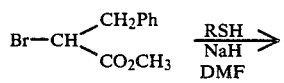

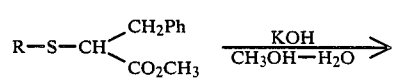

V

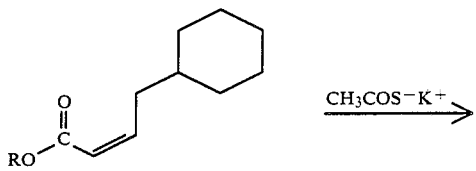

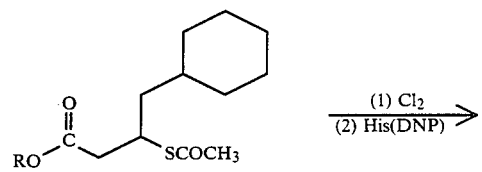

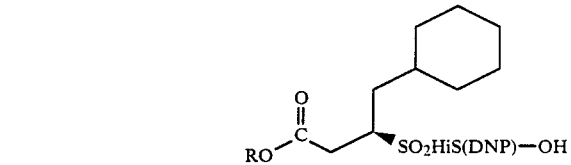

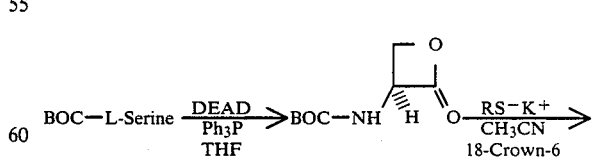

In the preparation of some of the inhibitors of the present invention, a protected form of the B-component may be an amino acid of the formula VI, which is prepared as illustrated in the schemes:

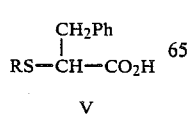

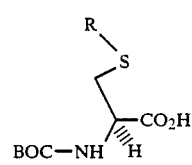

Arnold, et al, *J. Amer. Chem. Soc.*, 1985, 107, 7105–7109;

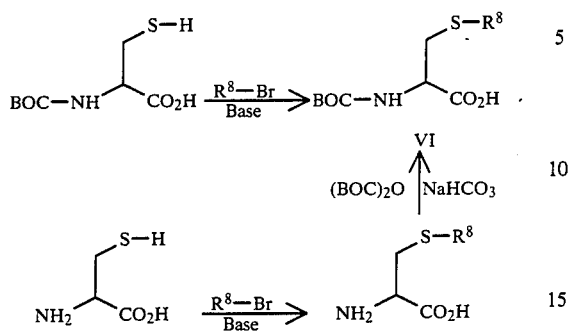

Frankel et al. *J. Chem. Soc.*, 1960, 1390; Akaburi et al, *Bull. Chem. Soc., Japan,* 1964, 37, 433; and Kornblum et al, *J. Amer. Chem. Soc.*, 1974, 96, 590; or

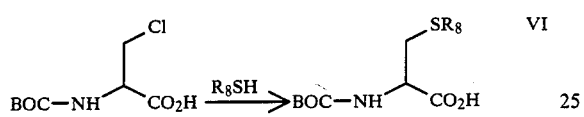

Melchior et al, *Arch. Biochem.*, 1947, 12, 301; and Wood et al, *J. Biol. Chem.*, 1949, 179, 529.

Preparation of some inhibitors of the present invention may require a protected form of the B component which is an amino acid of the formula VII or VIII, which are prepared as follows:

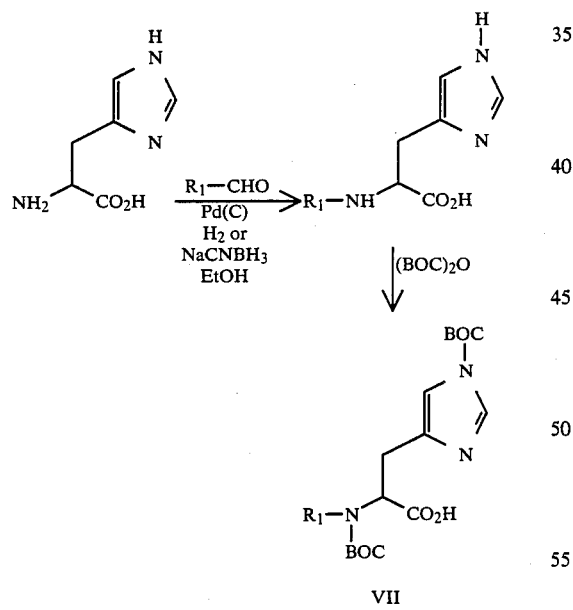

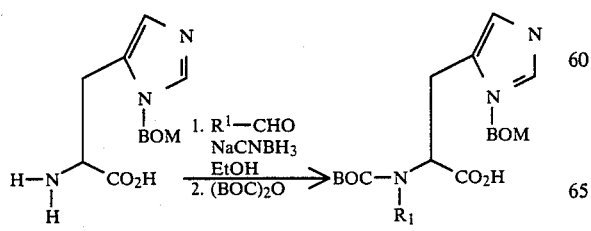

Stillwell et al, *Bioorganic Chem.*, 1975, 4, 317–325.

The A-B component of the present invention may consist of a urea moiety, for example, that is represented by formula IX, prepared as illustrated in the scheme:

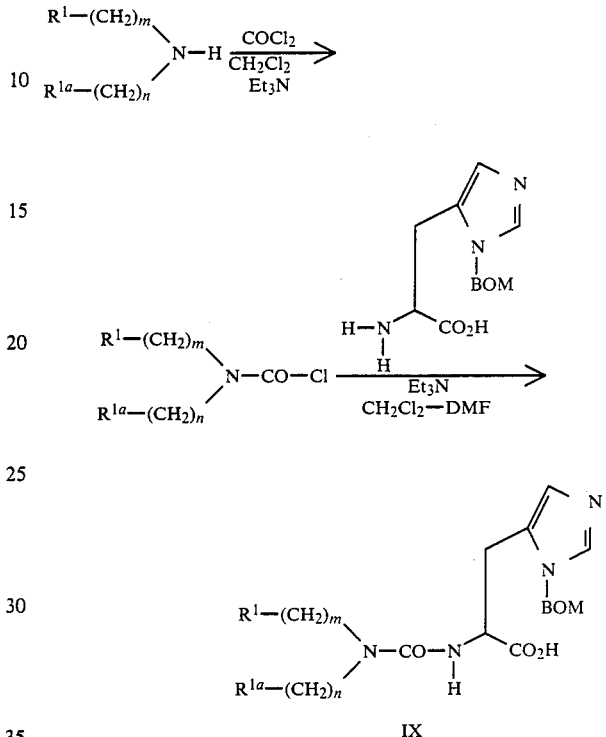

Alternatively, the A-B element may consist of a amide of, for example, formula X, the preparation of which is illustrated by the following:

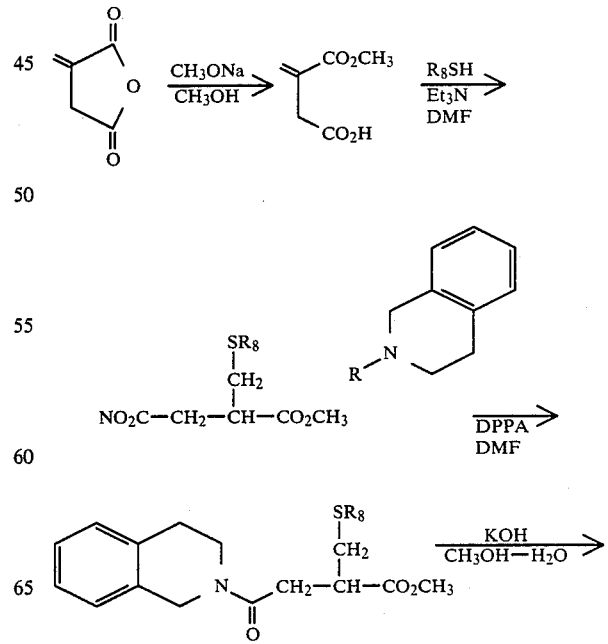

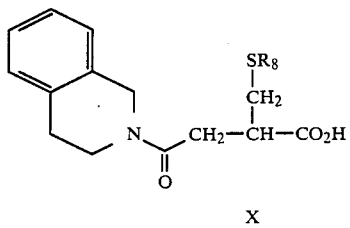

X

Peptides of Formula I which contain ACHPA as a peptide bond mimic are prepared using the following *procedures or similar procedures (as explained below)*:

In the following procedures, the amino acids represented by the elements B and T above are referred to as (respectively): $AA^1$ and $AA^3$.

In the following procedures, $RCO_2H$ is a carboxylic acid component where this component represents the A-B component of formula I. In this case, the B component is not an amino acid (i.e. the element K does not equal $NR^1$). The $R'CO_2H$ referred to below is a carboxylic acid component where this carboxylic acid represents the A component of formula I, where the B component of formula I represents and amino acid (i.e. K is equal to $NR^1$).

ROUTE A

Step A1

$BOC-AA^3$ (1) is coupled with an amine or alcohol component J, providing amide (or ester) 2. Amide (or ester) 2 may be treated with anhydrous TFA, giving 3. Additional reactive functional groups in the amino or alcohol component J are protected during the above steps (and those to follow below) with protecting groups, such as CBZ for amino groups, benzyl ethers for alcohols, and benzyl esters for carboxylic acids.

Step A2

BOC-ACHPA-OEt (4) is treated with anhydrous TFA to remove the BOC protecting group, giving ACHPA-OEt (5).

Step A3

Using standard methods, ACHPA-OEt (5) is coupled to $RCO_2H$, giving 8. Alternatively, an amino acid protected at the N-terminus with a BOC group ($BOC-AA^1$) is coupled to 5, giving a coupled product 6. The coupled product 6 is treated with anhydrous TFA to remove the Boc protecting group, and the resulting product 7 is coupled with $R'CO_2H$, giving 8a.

Step A4

The resulting coupled product 8 (or 8a) is treated with methanolic hydrazine, giving the corresponding hydrazide 9 (or 9a).

Step A5

Hydrazide 9 is treated with acidic isoamyl nitrite, producing the corresponding acyl azide, which is treated in situ with 3, giving coupled product 10 (or 10a). Alternatively, coupled product 8 is treated with sodium hydroxide in $THF-H_2O$ and the resulting carboxylic acid derivative coupled with J, giving 10 (or 10a). Direct coupling of 9 (or 9A) with the alcohol or amine component J gives the product 12 (or 12a).

Step A6

During the steps above, reactive functional groups present in the side-chains of amino acid components or in the J element are protected with protecting groups. These may be CBZ groups for amines, benzyl ethers for alcohols, and benzyl esters for carboxylic acids. In the case of histidine, the BOC protecting may be used for protection of the side-chain imidazole ring; this group is removed in step A4 during the treatment with hydrazine, or alternatively in step A5 during treatment with sodium hydroxide. Thereafter the histidine imidazole ring may be left unprotected.

Step A7

In cases where a quaternized amino group is to be introduced into the C-terminal J element of compound 11 (or 11a) or 13 (or 13a), one of the following procedures is followed to introduce the quaternized amine group:

Procedure 1

A tertiary amine within the J component is quaternized by treatment with an alkyl halide and $KHCO_3$ in methanol or ethanol, or with an alkyl halide in DMF. The resulting quaternary ammonium salt is then treated with anhydrous TFA to remove a BOC protecting group from an amine present in J, and the resulting free amine used for preparation of 3 as described in step A1 above. Likewise an amino acid $AA^3$, the side-chain of which contains a quaternary ammonium group, may be used for the preparation of 3.

Procedure 2

A compound 10 (or 10a) or 12 (or 12a), in which the J element or the side-chain of $AA^3$ contains a teriary amine, is prepared, and then the tertiary amine is quaternized by treatment with an alkyl halide in DMF. In this latter case, histidine, when present as the $AA^1$ element, must first be reprotected as the BOC derivative by treatment of 10 (or 10a) or 12 (or 12a) with di-t-butyldicarbonate. The BOC group is then removed after step A8 by treatment of 11 (or 11a) or 13 (or 13a) with $K_2CO_3$ in methanol or with anhydrous ammonia in DMF or methanol.

Step A8

Protecting groups are removed from 10 (or 10a) or 12 (or 12a) by hydrogenolysis, giving 11 (or 11a) or 13 (or 13a).

| Compound | Formula |
|---|---|
| 1 | $BOC-AA^3$ |
| 2 | $Boc-AA^3-J$ |
| 3 | $AA^3-J$ |
| 4 | BOC-ACHPA-OEt |
| 5 | ACHPA-OEt |
| 6 | $BOC-AA^1-ACHPA-OEt$ |
| 7 | $AA^1-ACHPA-OEt$ |
| 8 | RCO-ACHPA-OEt |
| 8a | $R'CO-AA^1-ACHPA-OEt$ |
| 9 | $RCO-ACHPA-NHNH_2$ |
| 9a | $R'CO-AA^1-ACHPA-NHNH_2$ |
| 10 (11) | $RCO-ACHPA-AA^3-J$ |
| 10a (11a) | $R'CO-AA^1-ACHPA-AA^3-J$ |
| 12 (13) | RCO-ACHPA-J |
| 12a (13a) | $R'CO-AA^1-ACHPA-J$ |

ROUTE B:

Step B1

BOC-ACHPA-OEt is treated with sodium hydroxide in THF-H$_2$O, giving BOC-ACHPA.

Step B2

BOC-ACHPA is coupled with 3, giving coupled product 14.

Step B3

Compound 14 is treated with anhydrous TFA to remove the BOC protecting group, giving 15.

Step B4

Compound 15 is coupled with RCO$_2$H, giving 10. Alternatively, 15 is coupled with BOC-AA$^1$, giving 16. Treatment of 16 with anhydrous TFA and coupling of the resulting product 17 with R'CO$_2$H gives 10a. Direct coupling of BOC-ACHPA with the amine or alcohol component J in step B2 and use of the procedures in steps B3 and B4 provides the products 12 (or 12a).

Step B5

In cases where a quaternized amino group is to be introduced into the C-terminal J element of compound 11 (or 11a) or 13 (or 13a), one of the following procedures is followed to introduce the quaternized amine group:

Procedure 1

A tertiary amine within the J element is quaternized by treatment with an alkyl halide and KHCO$_3$ in methanol or ethanol, or with an alkyl halide in DMF. The resulting quaternary ammonium salt is then treated with anhydrous TFA to remove a BOC protecting group from an amine present in J, and the resulting free amine used for the preparation of 3 as described in route A.

Procedure 2

A compound 10 (or 10a) or 12 (or 12a), in which AA$^3$ or the J element contains a teriary amine, is prepared and the tertiary amine is then quaternized by treatment with an alkyl halide in DMF. In this latter case, histidine, when present as the AA$^1$ element, must first be reprotected as the BOC derivative by treatment of 10 (or 10a) or 12 (or 12a) with di-t-butyldicarbonate. The BOC group is then removed after step B6 by treatment of 11 (or 11a) or 13 (or 13a) with K$_2$CO$_3$ in methanol or with anhydrous ammonia in DMF or methanol.

Step B6

As described above in route A, reactive functional groups in amino acid side chains of AA$^1$ and AA$_3$, and in the J component are protected during the coupling steps above. The protecting groups are now removed from coupled product 10 (or 10a) or 12 (or 12a) by hydrogenolysis giving compound 11 (or 11a) or 13 (or 13a).

| Compound | Formula |
|---|---|
| 14 | BOC—ACHPA—AA$^3$—J |
| 15 | ACHPA—AA$^3$—J |
| 10 (11) | RCO—ACHPA—AA$^3$—J |
| 16 | BOC—AA$^1$—ACHPA—AA$^3$—J |
| 17 | AA$^1$—ACHPA—AA$^3$—J |
| 10a (11a) | R'CO—AA$^1$—ACHPA—AA$^3$—J |
| 12 (13) | RCO—ACHPA—J |
| 12a (13a) | R'CO—AA$^1$—ACHPA—J |

Peptides of Formula I which contain statine are prepared as described above in routes A and B except that BOC-ACHPA-OEt is replaced with BOC-Sta-OEt. In this way, peptides such as 18, 19, 20 and 21 may be prepared.

| | |
|---|---|
| 18 | RCO—Sta—AA$^3$—J |
| 19 | RCO—Sta—J |
| 20 | R'CO—AA$^1$—Sta—AA$^3$—J |
| 21 | R'CO—AA$^1$—Sta—J |

Peptides of Formula I which contain amino-ACHPA (AmACHPA) or amino-statine (AmSta) are prepared as described above in Routes A and B except that BOC-ACHPA-OEt is replaced with BOC-AmACHPA(CBZ)-OEt or with BOC-AmSta(CBZ)-OEt. The CBZ group of the AmACHPA or AmSta element is removed by hydrogenolysis in step A8 or B6. In this way, peptide such as 22, 23, 24 and 25 (and the corresponding AmSta analogs) may be prepared.

| | |
|---|---|
| 22 | RCO—AmACHPA—AA$^3$—J |
| 23 | RCO—AmACHPA—J |
| 24 | R'CO—AA$^1$—AmACHPA—AA$^3$—J |
| 25 | R'CO—AA$^1$—AmACHPA—J |

Peptides of Formula I which contain a 2-substituted statine or ACHPA element as a peptide bond mimic may be prepared as described above in Routes A and B except that BOC-ACHPA-OEt is replaced with a suitably protected 2-substituted ACHPA or 2-substituted statine derivative, for example BOC-(2-allyl)ACHPA-OEt or BOC-(2-isobutyl)Sta-OEt. In this way, peptides such as 26, 27, 28, and 29 may be prepared.

| | |
|---|---|
| 26 | RCO—(2-isobutyl)ACHPA—AA$^3$—J |
| 27 | RCO—(2-isobutyl)ACHPA—J |
| 28 | R'CO—AA$^1$—(2-allyl)ACHPA—AA$^3$—J |
| 29 | R'CO—AA$^1$—(2-allyl)ACHPA—J |

Peptides of Formula I which contain Cal[CH(OH)CH$_2$]Val as a peptide bond mimic are prepared as described below in Routes C and D.

ROUTE C:

Step C1

The Boc protecting group is removed from lactone 25 by treatment with anhydrous TFA, giving lactone 26.

Step C2

Lactone 26 is coupled with RCO$_2$H, giving 27, or with a N-terminal Boc-protected amino acid (Boc-AA$^1$) giving 28. Treatment of 28 with anhydrous TFA and coupling of the product 29 with R'CO$_2$H yields 30.

Step C3

Lactone 27 (or 30) is treated with aqueous potassium hydroxide to give the corresponding hydroxyacid. The hydroxyacid is treated with t-butyldimethylsilyl chloride and imidazole, then with HOAc in THF-H$_2$O, giving the protected hydroxyacid 31 (32).

Step C4

Compound 31 (or 32) is coupled with 3, giving 33 (or 34). Additional reactive functional groups in the amino acid side-chains or in component J are protected with protecting groups such as CBZ for amino and guanidino groups, benzyl ethers for alcohols, and benzyl esters for carboxylic acids. When histidine is used as an amino acid component, the side-chain imidazole ring may be protected during step C2 with a BOC protecting group. This protecting group is removed during treatment with TFA, and the imidazole ring left unprotected during subsequent N-terminal coupling or acylation reactions. Alternatively histidine may be protected with a DNP protecting group during step C2. This group is then removed in step C3 during the potassium hydroxide treatment.

Step C5

The silyl protecting group is removed from 33 (34) by treatment with tetrabutylammonium fluoride in THF-DMF, giving 35 (36).

Step C6

In some cases, a quaternized amino group is present in the C-terminal J element of compound 37 (38). In this case, on the the following procedures is used:

*Procedure 1*

A tertiary amine within the J element is quaternized by treatment with an alkyl halide and KHCO$_3$ in methanol or ethanol or with an alkyl halide in DMF. The resulting quaternary ammonium salt is then treated with anhydrous TFA to remove a BOC protecting group from an amine function present in J, and the resulting free amine used for preparation of compound 3.

*Procedure 2*

A compound 35 (36) containing a tertiary amine in the J or AA$^3$ element is prepared. If histidine is present as the AA$^1$ component, the imidazole ring is protected next by treatment with di-t-butyldicarbonate and Et$_3$N in methanol or DMF. The tertiary amine present in the AA$^3$ or J element is then quaternized by treatment with an alkyl halide in DMF.

Step C7

Protecting groups are removed from 35 (36) by hydrogenolysis, gving 37 (38).

| | |
|---|---|
| 25 | BOC—Cal[CH(OH)CH$_2$]Val lactone |
| 26 | Cal[CH(OH)CH$_2$]Val lactone |
| 27 | ROC—Cal[CH(OH)CH$_2$]Val lactone |
| 28 | BOC—AA$^1$—Cal[CH(OH)CH$_2$]Val lactone |
| 29 | AA$^1$—Cal[CH(OH)CH$_2$]Val lactone |
| 30 | R'CO—AA$^1$—Cal[CH(OH)CH$_2$]Val lactone |
| 31 | RCO—Cal[CH(OTBDMS)CH$_2$]Val—OH |
| 32 | R'CO—AA$^1$—Cal[CH(OTBDMS)CH$_2$]Val—OH |
| 33 | RCO—Cal[CH(OTBDMS)CH$_2$]Val—AA$^3$—J |
| 34 | R'CO—AA$^1$—Cal[CH(OTBDMS)CH$_2$]Val—AA$^3$—J |
| 35 (37) | RCO—Cal[CH(OH)CH$_2$]Val—AA$^3$—J |
| 36 (38) | R'CO—AA$^1$—Cal[CH(OH)CH$_2$]Val—AA$^3$—J |

Using similar procedures, 39 and 40 may be prepared:

| | |
|---|---|
| 39 | RCO—Cal[CH(OH)CH$_2$]Val—J |
| 40 | R'CO—AA$^1$—Cal[CH(OH)CH$_2$]Val—J |

ROUTE D:

Step D1

Lactone 25 is treated with potassium hydroxide to give the corresponding hydroxyacid 41. The hydroxyacid 41 is treated with t-butyldimethylsilyl chloride and imidazole, then with HOAc in THF-H$_2$O, giving the protected hydroxyacid 42.

Step D2

Protected hydroxyacid 42 is coupled with 3, giving 43. Additional reactive functional groups in the J component are protected with protecting groups such as CBZ for amino and guanidino groups, benzyl ethers for alcohols, and benzyl esters for carboxylic acids.

Step D3

The BOC protecting group is removed from 43 by treatment with anhydrous TFA, giving 44.

Step D4

Compound 44 is coupled with RCO$_2$H giving compound 33 or with an amino acid bearing an N-terminal BOC protecting group (BOC-AA$^1$), giving coupled product 45.

Step D5

The N-terminal BOC protecting group is removed from 45 by treatment with anhydrous TFA, giving compound 46.

Step D6

Compound 46 is coupled with R'CO$_2$H, giving compound 34.

Step D7

Compounds 33 and 34 are treated as described above in route C, providing compounds 37 and 38.

Using procedures similar to those described above, compounds 39 and 40 may be prepared.

| | |
|---|---|
| 25 | BOC—Cal[CH(OH)CH$_2$]Val lactone |
| 41 | BOC—Cal[CH(CH)CH$_2$]Val—OH |
| 42 | BOC—Cal[CH(OTBDMS)CH$_2$]Val—OH |
| 43 | BOC—Cal[CH(OTBDMS)CH$_2$Val—AA$^3$—J |
| 44 | Cal[CH(OTBDMS)CH$_2$]Val—AA$^3$—J |
| 45 | BOC—AA$^1$—Cal[CH(OTBDMS)CH$_2$]Val—AA$^3$—J |
| 46 | AA$^1$—Cal[CH(OTBDMS)CH$_2$]Val—AA$^3$—J |

The novel peptides of the present invention possess an excellent degree of activity in treating hypertension and congestive heart failure in humans, as well as in other warm-blooded animals, such as mice, rats, horses, dogs, cats, etc., and they may be orally-active.

For these purposes the compounds of the present invention may be administered orally, parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The pharmaceutical compositions may be in the form of a sterile injectable preparation, for example, as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example, as a solution in 1,3-butanediol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The peptides of this invention may also be administered in the form of suppositories for rectal administration of the drug. These compositions may be prepared by mixing the drug with a suitable non-irritating excipient, such as cocoa butter or polyethylene glycols, which is solid at ordinary temperatures but liquid at the rectal temperature and will therefore melt in the rectum to release the drug.

Dosage levels of the order of 0.1 to 4.0 grams-per-day parenterally are useful in the treatment of the above indicated conditions, with oral doses three-to-ten times higher. For example, renin-associated hypertension and hyperaldosteronism are effectively treated parenterally by the administration of from 1.0 to 50 milligrams of the compound-per-kilogram of body weight per day. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The present invention is also directed to combinations of the novel enzyme-inhibitory peptides of Formula I with one or more antihypertensive agents selected from the group consisting of diuretics, α and/or β-adrenergic blocking agents, CNS-acting antihypertensive agents, adrenergic neuron blocking agents, vasodilators, angiotensin I converting enzyme inhibitors, calcium channel blockers and other antihypertensive agents.

For example, the compounds of this invention may be given in combination with such compounds or salt or other derivative forms thereof as:

*Diuretics:* acetazolamide; amiloride; bendroflumethiazide; benzthiazide; bumetanide; chlorothiazide; chlorothalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate; sodium nitroprusside; spironolactone; ticrynafen; triamterene; trichlormethiazide;

*α-Adrenergic Blocking Agents:* dibenamine; phentolamine; phenoxybenzamine; prazosin; tolazoline;

*β-Adrenergic Blocking Agents:* atenolol; metoprolol; nadolol; propranolol; timolol;

((±)-2-[3-(tert-butylamino)-2-hydroxypropoxy]-2-furananilide) (ancarolol);

(2-acetyl-7-(2-hydroxy-3-isopropylaminopropoxy)benzofuran HCl) (befunolol);

((±)-1-(isopropylamino)-3-(p-(2-cyclopropylmethoxyethyl)-phenoxy)-2-propranol HCl) (betaxolol);

(1-[(3,4-dimethoxyphenethyl)amino]-3-(m-tolyloxy)-2-propanol HCl) (bevantolol);

(((±)-1-(4-((2-isopropoxyethoxy)methyl)phenoxy)-3-isopropylamino-2-propanol)fumarate) (bisoprolol);

(4-(2-hydroxy-3-[4-(phenoxymethyl)-piperidino]-propoxy)-indole);

(carbazolyl-4-oxy-5,2-(2-methoxyphenoxy)-ethylamino-2-propanol);

(1-((1,1-dimethylethyl)amino)-3-((2-methyl-1H-indol-4-yl)oxy)-2-propanol benzoate) (bopindolol);

(1-(2-exobicyclo[2.2.1]-hept-2-ylphenoxy)-3-[(1-methylethyl)-amino]-2-propanol HCl) (bornaprolol);

(o-[2-hydroxy-3-[(2-indol-3-yl-1,1-dimethylethyl)amino]propoxy]benzonitrile HCl) (bucindolol);

(α-[(tert.butylamino)methyl]-7-ethyl-2-benzofuranmethanol) (bufuralol);

(3-[3-acetyl-4-[3-(tert.butylamino)-2-hydroxypropyl]-phenyl]-1,1-diethylurea HCl) (celiprolol);

((±)-2-[2-[3-[(1,1-dimethylethyl)amino]-2-hydroxypropoxy]phenoxy]-N-methylacetamide HCl) (cetamolol);

(2-benzimidazolyl-phenyl(2-isopropylaminopropanol));

((±)-3'-acetyl-4'-(2-hydroxy-3-isopropylaminopropoxy)(methyl-4-[2-hydroxy-3-[(1-methylethyl)amino-propoxy]]benzenepropanoate HCl) (esmolol);

(erythro-DL-1-(7-methylindan-4-yloxy)-3-isopropylaminobutan-2-ol);

(1-(tert.butylamino)-3-[O-(2-propynyloxy)phenoxy]-2-propanol (pargolol);

(1-tert.butylamino)-3-[o-(6-hydrazino-3-pyridazinyl)-phenoxy]-2-propanol diHCl) (prizidilol);

((−)-2-hydroxy-5-[(R)-1-hydroxy-2-[(R)-(1-methyl-3-phenylpropyl)amino]ethyl]benzamide);

(4-hydroxy-9-[2-hydroxy-3-(isopropylamino)-propoxy]-7-methyl-5H-furo[3,2-g][1]-benzopyran-5-one) (iprocrolol);

((−)-5-(tert.butylamino)-2-hydroxypropoxy]-3,4-dihydrol-1-(2H)-naphthalenone HCl) (levobunolol);

(4-(2-hydroxy-3-isopropylamino-propoxy)-1,2-benzisothiazole HCl);

(4-[3-(tert.butylamino)-2-hydroxypropoxy]-N-methylisocarbostyril HCl);

((±)-N-2-[4-(2-hydroxy-3-isopropyl aminopropoxy)-phenyl]ethyl-N'-isopropylurea) (pafenolol);

(3-[[(2-trifluoroacetamido)ethyl]amino]-1-phenoxypropan-2-ol);

(N-(3-(o-chlorophenoxy)-2-hydroxypropyl)-N'-(4'-chloro-2,3-dihydro-3-oxo-5-pyridazinyl)ethylenediamine);

((±)-N-[3-acetyl-4-[2-hydroxy-3-[(1-methylethyl)amino]propoxy]phenyl]butanamide) (acebutolol);

((±)-4'-[3-(tert-butylamino)-2-hydroxypropoxy]spiro[cyclohexane-1,2'-indan'-1]-one) (spirendolol);

(7-[3-[[2-hydroxy-3-[(2-methylindol-4-yl)oxy]propyl]amino]butyl]thiophylline) (teoprolol);

((±)-1-tert.butylamino-3-(thiochroman-8-yloxy)-2-propanol) (tertatolol);

((±)-1-tert.butylamino-3-(2,3-xylyloxy)-2-propanol HCl) (xibenolol);

(8-[3-(tert.butylamino)-2-hydroxypropoxy]-5-methylcoumarin (bucumolol);

(2-(3-(tert.butylamino)-2-hydroxy-propyl)benzonitrile HCl) (bunitrolol);

((±)-2'-[3-(tert-butylamino)-2-hydroxypropoxy-5'-fluorobutyrophenone) (butofilolol);
(1-(carbazol-4-yloxy)-3-(isopropylamino)-2-propanol) (carazolol);
(5-(3-tert.butylamino-2-hydroxy)propoxy-3,4-dihydrocarbostyril HCl) (carteolol);
(1-(tert.butylamino)-3-(2,5-dichlorophenoxy)-2-propanol) (cloranolol);
(1-(inden-4(or 7)-yloxy)-3-(isopropylamino)-2-propanol HCl) (indenolol);
(1-isopropylamino-3-[2-methylindol-4-yl)oxy]-2-propanol) (mepindolol);
(1-(4-acetoxy-2,3,5-trimethylphenoxy)-3-isopropylaminopropan-2-ol) (metipranolol);
(1-(isopropylamino)-3-(o-methoxyphenoxy)-3-[(1-methylethyl)amino]-2-propanol) (moprolol);
((1-tert.butylamino)-3-[(5,6,7,8-tetrahydro-cis-6,7-dihydroxy-1-naphthyl)oxy]-2-propanol) (nadolol);
((S)-1-(2-cyclopentylphenoxy)-3-[(1,1-dimethylethyl)amino]-2-propanol sulfate (2:1)) (penbutolol);
(4'-[1-hydroxy-2-(amino)ethyl]methanesulfonanilide) (sotalol);
(2-methyl-3-[4-(2-hydroxy-3-tert.butylaminopropoxy)-phenyl]-7-methoxy-isoquinolin-1-(2H)-one);
(1-(4-(2-(4-fluorophenyloxy)ethoxy)phenoxy)-3-isopropylamino-2-propanol HCl);
((−)-p-[3-[(3,4-dimethoxyphenethyl)amino]-2-hydroxypropoxy]-β-methylcinnamonitrile) (pacrinolol);
((±)-2-(3'-tert.butylamino-2'-hydroxypropylthio)-4-(5'-carbamoyl-2'-thienyl)thiazole HCl) (arotinolol);
((±)-1-[p-[2-(cyclopropylmethoxy)ethoxy]phenoxy]-3-(isopropylamino)-2-propanol) (cicloprolol);
((±)-1-[(3-chloro-2-methylindol-4-yl)oxy]-3-[(2-phenoxyethyl)amino]-2-propanol) (indopanolol);
((±)-6-[[2-[[3-(p-butoxyphenoxy)-2-hydroxypropyl]amino]ethyl]amino]-1,3-dimethyluracil) (pirepolol);
(4-(cyclohexylamino)-1-(1-naphtholenyloxy)-2-butanol);
(1-phenyl)-3-[2-[3-(2-cyanophenoxy)-2-hydroxypropyl]aminoethyl]hydantoin HCl);
(3,4-dihydro-8-(2-hydroxy-3-isopropylaminopropoxy)-3-nitroxy-2H-1-benzopyran) (nipradolol);

α and β-Adrenergic Blocking Agents ((±)-1-tert-butylamino)-3-[o-[2-(3-methyl-5-isoxazolyl)vinyl]phenoxy]-2-propanol) (isoxaprolol);
(1-isopropylamino-3-(4-(2-nitroxyethoxy)phenoxy)-2-propanol HCl);
(4-hydroxy-α-[[3-(4-methoxyphenyl)-1-methylpropyl]aminomethyl]-3-(methylsulfinyl)-benzmethanol HCl) (sulfinalol);
(5-[1-hydroxy-2-[[2-(o-methoxyphenoxy)ethyl]amino]ethyl]-2-methylbenzenesulfonamide HCl);
(5-[1-hydroxy-2-[(1-methyl-3-phenylpropyl)amino]ethyl]salicylamide HCl) (labetalol);
(1-((3-chloro-2-methyl-1H-indol-4-yl)oxy)-3-((2-phenoxyethyl)amino)-2-propanol-hydrogenmalonate) (ifendolol);
(4-(2-hydroxy-3-[(1-methyl-3-phenylpropyl)amino]propoxy)benzeneacetamide);
(1-[3-[[3-(1-naphthoxy)-2-hydroxypropyl]-amino]-3,3-dimethyl-propyl]-2-benzimidazolinone);
(3-(1-(2-hydroxy-2-(4-chlorophenylethyl)-4-piperidyl)-3,4-dihydroxy)quinoxalin-2(1H)-one);

*CNS-Acting Agents:* clonidine; methyldopa;
*Adrenergic Neuron Blocking Agents:* guanethidine; reserpine and other rauwolfia alkaloids such as rescinnamine;

*Vasodilators:* diazoxide; hydralazine; minoxidil;
*Angiotensin I Converting Enzyme Inhibitors:*
1-(3-mercapto-2-methyl-1-oxopropyl)-L-proline (captopril);
(1-(4-ethoxycarbonyl-2,4(R,R)-dimethylbutanoyl)indoline-2(S)-carboxylic acid);
(2-[2-[[1-(ethoxycarbonyl)-3-phenyl-propyl]amino]-1-oxopropyl]-1,2,3,4-tetradhydro-3-isoquinoline carboxylic acid);
((S)-1-[2-[[1-(ethoxycarbonyl)-3-phenylpropyl]amino]-1-oxopropyl]octahydro-1H-indole-2-carboxylic acid HCl);
(N-cyclopentyl-N-(3-(2,2-dimethyl-1-oxopropyl)thiol-2-methyl-1-oxopropyl)glycine) (pivalopril);
((2R,4R)-2-(2-hydroxyphenyl)-3-(3-mercaptopropionyl)-4-thiazolidinecarboxylic acid);
(1-(N-[1(S)-ethoxycarbonyl-3-phenylpropyl]-(S)-alanyl)cis,syn-octahydroindol-2-(S)-carboxylic acid HCl);
((−)-(S)-1-[(S)-3-mercapto-2-methyl-1-oxopropyl]indoline-2-carboxylic acid);
([1(S),4S]-1-[3-(benzoylthio)-2-methyl-1-oxopropyl]-4-phenylthio-L-proline;
(3-([1-ethoxycarbonyl-3-phenyl-(1S)-propyl]amino)-2,3,4,5-tetrahydro-2-oxo-1-(3S)-benzazepine-1-acetic acid HCl);
(N-(2-benzyl-3-mercaptopropanoyl)-S-ethyl-L-cysteine) and the S-methyl analogue;
(N-(1(S)-ethoxycarbonyl-3-phenylpropyl)-L-alanyl-L-proline maleate) (enalapril);
N-[1-(S)-carboxy-3-phenylpropyl]-L-alanyl-1-proline;
N²-[1-(S)-carboxy-3-phenylpropyl]-L-lysyl-L-proline (lysinopril);
2-[N-[(S)-1-ethoxycarbonyl-3-phenylpropyl]-L-alanyl-(1S,3S,5S)-2-azabicyclo[3.3.0]octane-3-carboxylic acid;
[1(S),4S]-1-(3-mercapto-2-methyl-1-oxopropyl)-4-phenylthio-L-proline S-benzoyl calcium salt (zofenopril);
[1-(+/−)4S]-4-cyclohexyl-1-[[2-methyl-1-[1-propoxy)propoxy](4-phenylbutyl)phosphinyl]acetyl]-L-proline sodium salt (fosfopril).

*Calcium Channel Blockers:* nifedepine; nitrendipine, verapamil; diltiazam.
*Other Antihypertensive Agents:* aminophylline; cryptenamine acetates and tannates: deserpidine; meremethoxylline procaine; pargyline; trimethaphan camsylate; and the like, as well as admixtures and combinations thereof.

Typically, the individual daily dosages for these combinations can range from about one-fifth of the minimally-recommended clinical dosages to the maximum-recommended levels for the entities when they are given singly. Coadministration is most readily accomplished by combining the active ingredients into a suitable unit dosage form containing the proper dosages of each. Other methods of coadministration are, of course, possible.

The following Examples are intended to be representative and not limiting.

EXAMPLE 1

Preparation of Boc-ACHPA-NH-2(S)-methylbutyl

A. BOC-ACHPA-OH

Four grams of BOC-ACHPA-OEt was dissolved in methanol (15 mL) and H₂O (5 mL) and the pH was adjusted to 10 with 1:1 pH 10 buffer: CH₃OH. To the solution was added 2N NaOH (2.1 equiv) and the mixture allowed to stir for 2 hours. The pH was again adjusted to 10 by the addition of 1N HCl, and the solution extracted with EtOAc. The solution was then cooled in ice, EtOAc was added, and the aqueous layer was acidified to pH 2.5 by addition of 6N HCl. The organic layer and several EtOAc extracts of the aqueous layer were combined, dried (Na$_2$SO$_4$) and evaporated to 3.5 g (93%) of a white brittle foam. TLC (silica gel; 80:10:1:1 CHCl$_3$:CH$_3$OH:H$_2$O:HOAc) shows a single spot, Rf=0.45.

B. BOC-ACHPA-NH-2(S)-methylbutyl

To a cooled (ice-bath) solution of BOC-ACHPA-OH (3.5 g) in DMF (25 mL) was added Et$_3$N (1.6 mL) and DPPA (2.5 mL), with the resulting mixture being stirred under nitrogen for 30 minutes, before 2(S)-methylbutylamine (1.36 ml) was added. The reaction mixture was stirred and allowed to warm to room temperature. After 18 hours, the mixture was concentrated in vacuo and the residue taken up in EtOAc (250 mL). The solution was washed with 1N HCl, H$_2$O, saturated NaHCO$_3$, H$_2$O and brine and then dried (Na$_2$SO$_4$), with the residue after evaporation being purified by chromatography on silica gel (6:4 hexanes:EtOAc), to give BOC-ACHPA-NH-(2(S)-methylbutyl) (3.75 g; 89%) as a colorless oil.

EXAMPLE 2

Preparation of 3-Isopropylsulfonyl-2-benzylpropionic Acid

To a solution of methyl-2-benzylacrylate (20 gm, 0.113 mol) in methanol (100 ml) at room temperature was added a solution of sodium methoxide (2N, 17 ml) followed by isopropylthiol (12.56 ml). TLC (4:1, Hexanes: ethyl acetate) showed reaction to be complete after 30 min. The reaction mixture was made acidic with 1N HCl and extracted three times with ethyl acetate. The combined organic fractions were dried over NaSO$_4$, filtered and evaporated in vacuo. The crude product was purified by chromatography (silica 4:1, hexanes: ethyl acetate to give methyl-3-isopropylthio-2-benzylpropionate.

To the aforementioned compound in chloroform at 0° C. was added m-Chloroperoxybenzoic acid (45 gm, 0.339 mol) portionwise and the reaction was stirred 48 hr at room temperature. When TLC (silica, 1:1 hexanes:ethyl acetate) showed reaction to be complete, the reaction mixture was filtered and the filtrate was thoroughly washed with sat. NaHCO$_3$, dried over NaSO$_4$, filtered and evaporated in vacuo.

The crude product was chromatographed (silica, 1:1, hexanes:ethyl acetate) to give 30 gm of methyl-3-isopropylsulfonyl-2-benzylpropionate. TLC (silica, 1:1, hexanes:ethyl acetate) Rf=0.50. NMR (CDCl$_3$) 1.3 (d, 3H), 1.35 (d, 3H), 2.8-3.0 (m, 2H), 3.0-3.15 (m, 2H), 3.3-3.4 (m, 1H), 3.4-3.5 (m, 1H), 3.7 (s, 1H), 7.15-7.35 (m, 5H).

The above ester was stirred 12 hr at 60° C. in a solution of HOAc (20 ml) and concentrated HCl (100 ml). The reaction mixture was then cooled and extracted three times with ethyl acetate. The combined organic fractions were dried over NaSO$_4$, filtered and evaporated in vacuo. The resulting carboxylic acid (23 gm) was resolved in diethyl ether (400 ml) using R(+)methylbenzylamine to give the (+) isomer. [α]$_D$-MeOH = +11°. NMR (CDCl$_3$) 1.3 (d, 3H), 1.35 (d, 3H), 2.9-3.1 (m, 4H), 3.23 (m, 1H), 3.35-3.45 (m, 1H), 7.2-7.4 (m, 5H).

EXAMPLE 3

3-Cyclohexylsulfonyl-2-benzylpropionic Acid

This compound was prepared according to procedures found in example 2. MS, m/e=310(M+). NMR (CDCl$_3$) 1.1-1.125 (m, 3H), 1.25-1.55 (m, 2H), 1.6-1.75 (brs, 1H), 1.8-2.0 (m, 4H), 2.05-2.15 (d, 1H), 2.7-2.85 (dt, 1H), 2.9-3.05 (m, 2H), 3.15-3.3 (dd, 1H), 3.3-3.5 (m, 2H), 7.2-7.4 (m, 5H).

EXAMPLE 4

3-N-morpholinocarbonyl-2(R)-(1-naphthylmethyl)propionic Acid

A.

Methyl-3-carboxy-2(R)-(1-naphthylmethyl)propionic Acid

To solution of potassium (2.15 gm) in t-butanol (45 ml) at room temperature was added dropwise a solution of dimethylsuccinate (14 ml) and 1-naphthaldehyde (7.5 ml). The reaction mixture was then heated to reflux for a period of 30 min. whereupon, it was cooled to 0° C. The reaction mixture was made acidic with HCl (6N, 10 ml) and evaporated in vacuo. The reaction mixture was partitioned between water and diethyl ether and the combined organic fractions were extracted with NH$_4$OH (1N) four times. The combined basic fractions were washed with diethyl ether, and acidified with HCl (3N), and extracted thoroughly with methylene chloride. The combined organic fractions were dried over Na$_2$SO$_4$, filtered and evaporated in vacuo. Without purification the crude methyl-4-carboxy-2-(1-naphthylmethylene)-propionate was dissolved in methanol (100 ml) and to this solution at 0° C. slowly added magnesium turnings (2.3 gm) over a 3 hr period. When all the magnesium had been consumed, the reaction mixture was poured into HCl (carefully, 3N, 150 ml). The reaction mixture was extracted with diethyl ether, dried over Na$_2$SO$_4$, filtered and evaporated in vacuo to give the title compound in its racemic form. This material has been resolved with (+) methylbenzylamine in diethyl ether. Thus 5.2 gm of racemic material has been converted to 2.2 gm of pure R(+) title compound. [α]$_D$=+48.56 (EtOAc). NMR (CDCl$_3$) 2.4-2.5 (dd, 1H), 2.7-2.85 (2d, 1H), 3.05-3.15 (ABq, 1H), 3.55-3.7 (m, 1H), 3.7 (S, 3h), 7.27 (d, 1H), 7.3-7.4 (t, 1H), 7.45-7.6 (m, 2H), 7.75 (d, 1H), 7.85 (d, 1H), 8.05 (d, 1H).

B.

3-morpholinocarbonyl-2-(1-naphthylmethyl)propionic Acid

To a solution of the aforementioned acid (1 gm, 0.0037 mol), morpholine (0.64 ml, 2 equiv.), and 1-hydroxybenzotriazole (0.6 gm) in methylene chloride at 0° C. was added dicyclohexylcarbodiimide (0.92 gm). The reaction was stirred 12 hr at which time it was filtered. The filtrate was washed with HCl (1N), sat. NaHCO$_3$, dried over Na$_2$SO$_4$, filtered and evaporated in vacuo. The crude product was chromatographed (silica, 7:3 EtOAc:hexanes) to give the methyl ester of the title compound TLC (silica, 7:3 EtOAc:hexanes) Rf=0.46. To a solution of this material in methanol (1 ml) was added a solution of KOH (1N, 6.45 ml). After 3 hr the reaction mixture was made acidic with HCl (3N) and extracted twice with EtOAc. The combined organic fractions were dried over Na$_2$SO$_4$, filtered and evaporated in vacuo to give the title compound (0.78 gm). NMR (CDCl$_3$) 2.4–2.5 (dd, 1H), 2.6–2.7 (2d, 1H), 3.1–3.3 (m, 4H), 3.3–3.4 (m, 1H), 3.45–3.7 (m, 5H), 3.7–3.8 (dd, 1H), 7.3 (d, 1H), 7.4 (t, 1H), 7.45–7.6 (m, 2H), 7.75 (d, 1H), 7.85 (d, 1H), 8.1 (d, 1H).

EXAMPLE 5

3-N-morpholinocarbonyl-2(R)-benzylpropionic Acid

A. Methyl-3-carboxy-2(R)-benzylpropionic Acid

This compound was prepared by a procedure similar to example 4A. [α]$_D$= +22.9 (MeOH). NMR (CDCl$_3$) 2.4–2.5 (dd, 1H), 2.65–2.85 (m, 2H), 3.05–3.2 (m, 2H), 7.15–7.4 (m, 5H).

B. 3-N-morpholinocarbonyl-2(R)-benzylpropionic Acid

The title compound was prepared according to procedures outlined in example 4B. NMR (CDCl$_3$) 2.3–2.4 (dd, 1H), 2.6–2.7 (2d, 1H), 2.7–2.85 (ABq, 1H), 3.15–3.3 (m, 2H), 3.3–3.4 (m, 2H), 3.5–3.8 (m, 6H), 7.15–7.35 (m, 5H).

EXAMPLE 6

(4-Boc-piperazin-1-yl)carbonyl-2(R)benzylpropionic Acid

This compound was prepared according to procedures outlined in example 4 using N-Boc-piperazine. NMR (CDCl$_3$) 1.45 (s, 9H), 2.32–2.4 (dd, 1H), 2.6–2.7 (m, 1H), 2.7–2.85 (m, 1H), 3.15–3.45 (m, 8H), 3.5–4.2 (m, 2H), 7.15–7.4 (m, 5H).

EXAMPLE 7

Preparation of 3-(4-Boc-Piperazin-1-yl)Carbonyl-2(RS)-(1-Naphthyl)-Methylpropionic Acid This compound was prepared according to procedures found in Example 4. NMR (CDCl$_3$) 1.5 (s, 9H), 2.43–2.55 (dd, 1H), 2.6–2.7 (2d, 1H), 3.1–3.3 (m, 5), 3.3–3.45(m, 3H), 3.45–3.645 (m, 2H), 3.7–3.8 (dd, 1H), 7.3 (d, 1H), 7.4 (t, 1H), 7.45–7.6 (m, 2H), 7.75 (d, 1H), 7.85 (d, 1H), 8.1 (d, 1H).

EXAMPLE 8

Preparation of 3-(Thiamorpholin-1-yl)Carbonyl-2(RS)-(1-Naphthyl)-Methylpropionic Acid This compound was prepared by procedures found in Example 4. NMR 2.2–2.5 (dd, 1H), 2.5–2.7 (m, 3H), 3.15–3.25 (ABq, 1H), 3.3–3.45 (m, 2H), 3.45–3.6 (m, 2H), 3.7–3.9 (m, 4H), 7.3 (d, 1H), 7.4 (t, 1H), 7.5–7.6 (m, 2H), 7.8 (d,1H), 7.9 (d, 1H), 8.1 (d, 1H).

EXAMPLE 9

Boc-(im-DNP)His-ACHPA-NH-2(S)-Methylbutyl

Boc-ACHPA-NH-2(S)-methylbutyl (0.85 gm, 0.0022 mol) was dissolved in a saturated solution of HCl in methanol and the reaction was allowed to stir for 1 hr at which time it was thoroughly evaporated in vacuo. To the amine hydrochloride in methylene chloride (10 ml) at 0° C. was added triethylamine (1 ml, 3 equiv.). After 15 min., Boc-N-im-DNP-histidine (1 gm, 1.1 equiv.) was added to the solution followed by 1-hydroxybenzotriazole hydrate (0.326 gm) and dicylcohexylcarbodiimide (0.5 gm). Reaction was slowly warmed to room temperature and stirred until reaction was complete (12 hr). The reaction mixture was filtered to remove dicyclohexylurea and the filtrate was successively washed with 1N HCl (twice), sat. NaHCO$_3$ (twice), dried over Na$_2$SO$_4$, filtered and evaporated in vacuo. The product was purified (Chromatography, silica, EtOAc) to give the title compound (1 gm). TLC (silica, EtOAc) Rf=0.68. NMR (CDCl$_3$) 0.85–0.95 (m, 6H), 1.0–1.3 (m, 6H), 1.3–1.7 (m, 9H), 1.4 (s, 9), 1.7–1.8 (d, 1H), 2.18–2.25 (dd, 1H), 2.35–2.45 (m, 1H), 3.0–3.2 (m, 4H), 3.85–4.0 (2H), 4.35–4.45 (ABq, 1H), 6.2 (brd, 1H), 6.48 (brt, 1H), 6.55 (d, 1H), 6.95 (s, 1H), 7.65 (s, 1H), 7.75 (d, 1H), 8.6 (dd, 1H), 8.85 (dd, 1H).

EXAMPLE 10

N-[3-morpholin-4-yl)carbonyl-2(R)-benzylpropionyl]-His-ACHPA-NH-2(S)-methylbutyl

A.

N-[3-(morpholin-4-yl)carbonyl-2(R)-benzylpropionyl]-(N-im-DMP)His-ACHPA-NH-2(S)methylbutyl Boc-(N-im-DNP)His-ACHPA-2(S)methylbutyl amide (0.3 gm, 0.000436 mol) in a saturated solution of HCl in MeOH was stirred 1 hr at rt whereupon the solution was thoroughly evaporated in vacuo. To this in methylene chloride (5 ml) with diisopropylethylamine (0.3 ml), 3-(morpholin-4-yl)carbonyl-2(R)-benzylpropionic acid (0.12 gm) was added benzotriazol-1-yloxytris(dimethylamino)phosphoniumhexafluorophosphate ("BOP") (0.23 gm, 1.2 equiv.). This reaction was stirred 12 hr at rt whereupon it was evaporated in vacuo, redissolved in EtOAc and washed with HCl (1N), and sat. NaHCO$_3$. The EtOAc solution was dried over Na$_2$SO$_4$, filtered and evaporated in vacuo. The product was chromatographed (silica, 9:1:0.5 EtOAc:Acetonitrile:-MeOH) to give the title compound (0.11 gm). TLC (silica, 9:1:0.5 EtOAc:acetonitrile:MeOH) Rf=0.53

B.

N-[3-morpholin-4-yl)carbonyl-2(R)-benzylpropionyl]-His-ACHPA-NH-(2(S)methylbutyl To a solution of the product of Example A in methanol (1 ml) was added thiophenol (0.05 ml). After stirring for 1 hr the reaction mixture was thoroughly evaporated. The product was chromatographed (LH-20, MeOH) to give the title compound (0.045 gm). TLC (silica, 85:15 EtOAc:MeOH) Rf=0.25. MS, m/e=682 (M+2), NMR consistent with structure.

EXAMPLE 11

N-[3-morpholin-4-yl)carbonyl-2(R)-(1-naphthyl)methylpropionyl]-His-ACHPA-NH-2(S)methylbutyl The title compound was prepared according to procedures found in Example 10. HPLC (RP-18, 8:2 MeOH:H$_2$O) rt=16.3 min. MS, m/e=731 (M+1). NMR consistent with compound.

EXAMPLE 12

N-[3-(thiamorpholin-4-yl)carbonyl-2(RS)-(1-naphthyl)-methylpropionyl]-His-ACHPA-NH-2(S)-methylbutyl This compound was prepared according to Example 10. MS, m/e=747 (M+1). HPLC (RP-18, 55:45 0.1% TFA:acetonitrile) rt=15.18 min. NMR consistent with compound.

EXAMPLE 13

N-[3-(4-Boc-piperazin-1-yl)Carbonyl-2(R)-Benzylpropionyl]-His-ACHPA-NH-2(S)-Methylbutyl This compound was prepared according to procedures of Example 10 using 3-(4-Boc-piperazin-1-yl)carbonyl-2(R)-benzylpropionic acid from Example 6. HPLC (RP-18, 70:30 MeOH:H$_2$O) rt=26.3 min. MS, m/e=680(M+1). NMR consistent with compound.

EXAMPLE 14

N-[3-(4-Boc-piperazin-1-yl)Carbonyl-2-(1-naphthyl)-Methylpropionyl]-His-ACHPA-NH-2(S)-Methylbutyl This compound was prepared according to procedures of Example 10 using 3-(4-Boc-piperazin-1-yl)carbonyl-2-(1-naphthyl)methylpropionic acid found in Example 7. MS, m/e=830(M+1). NMR consistent with compound.

EXAMPLE 15

N-[3-(piperazin-1-yl)Carbonyl-2-(1-naphthyl)Methylpropionyl]-His-ACHPA-NH-2(S)-Methylbutyl This compound was prepared according to procedures of Example 10. MS, m/e=730(M+1). NMR consistent with compound.

EXAMPLE 16

N-[3-Isopropylsulfonyl-2-Benzylpropionyl]-His-ACHPA-NH-2(S)-Methylbutyl

This compound was prepared according to procedures of Example 10 using 3-isopropylsulfonyl-2-benzylpropionic acid. MS, m/e=674(M+1). NMR is consistent with compound. HPLC (RP-18, 85:15, MeOH:H$_2$O) rt=10.48 min.

EXAMPLE 17

N-[3-Cyclohexylsulfonyl-2-Benzylpropionyl]-His-ACHPA-Lys-NHCH$_2$(pyridin-4-yl)

This compound was prepared by procedures of Example 10 using 3-cyclohexylsulfonyl-2-benzylpropionic acid. MS, m/e=714(M+1). NMR consistent with compound. HPLC (RP-18, 80:20 MeOH:H$_2$O).

EXAMPLE 18

N-[3-Isopropylsulfonyl-2-Benzylpropionyl]-His-ACHPA-Lys-NHCH$_2$(pyridin-4-yl)

Step A

N-[3-isopropylsulfonyl-2-benzylpropionyl]-His-ACHPA-(N$^\epsilon$-CBZ)Lys-NHCH$_2$(pyridin-4-yl)

A solution of Boc-(N-im-DNP)His-ACHPA-(N$^\epsilon$-CBZ)Lys-NHCH$_2$(pyridin-4-yl) (0.515 gm, 0.00053 mol) in methanol (20 ml) was saturated with HCl gas and stirred 30 min. at 0° C. The resulting amine hydrochloride was evaporated to dryness. To this material in methylene chloride at room temperature was added Diisopropylethylamine (0.546 ml, 6 equiv.), (+)-3-isopropylsulfonyl-2-benzylpropionic acid (0.157 gm, 1.1 equiv.) and Benzotriazol-1-yloxytris-(dimethylamino)-phosphoniumhexa fluorophosphate (0.28 gm, 1.2 equiv.). This reaction was stirred for 12 hr at which time it was washed once with 1N HCl, two times with sat. NaHCO$_3$, over NaSO$_4$, filtered through a thin pad of silica and evaporated to dryness. The crude intermediate [TLC (silica, 9:1:1 EtOAc:MeOH:acetonitrile)Rf=0.60] was redissolved in methylene chloride (10 ml) and to it was added thiophenol (0.25 ml) and the reaction mixture was stirred for 4 hr at which time it was thoroughly evaporated in vacuo. This material was chromatographed (LH-20, MeOH) to give the title compound (0.17 gm) as a solid. TLC (silica, 40:10:1 CHCl$_3$:MeOH:NH$_3$) Rf=0.4. HPLC (RP-18, 1:1 MeOH:0.1% TFA) rt=12 min. (95%). FAB mas spectral data: 957(M+H)

Step B

N-[3-isopropylsulfonyl-2-benzylpropionyl]-His-ACHPA-Lys-NHCH$_2$(pyridin-4-yl)

To a solution of the aforementioned compound (0.075 gm) in methanol (1 ml) at 0° C. was added a solution of HBr (30%) in acetic acid. The reaction was stirred 15 min. at yhis temperature and 20 min. at room temperature whereupon the the reaction was thoroughly evaporated to dryness. The residue was redissolved in MeOH (1 ml) and diluted with 20 ml of propylene oxide to give a white hygroscopic solid. This material was purified by HPLC (RP-18, 1:1 MeOH:0.1%TFA) rt=7.82 min. FAB mass spectral data: 823 (M+H).

EXAMPLE 19

N-[3-isopropylsulfonyl-2-Benzylpropionyl]-His-ACHPA-Lys-NHCH$_2$(piperidin-4-yl)

A solution of N-[3-isopropylsulfonyl-2-benzylpropionyl]-His-ACHPA-Lys-NHCH$_2$(piperidin-4-yl) (0.2 gm, 0.00021 mol) in MeOH (3 ml) and HCl (12N, 0.07 ml) and palladium hydroxide on carbon (20%, 0.1 gm) was hydrogenated for 24 hr at 40 lb. H$_2$ until NMR showed complete reduction of the pyridine group. The reaction mixture was filtered and evaporated in vacuo to give the title compound as the hydrochloride salt. FAB mass spectral data: 829 (M+H). NMR consistent with compound.

EXAMPLE 20

N-[3-isopropylsulfonyl-2-benzylpropionyl]-Nle-ACHPA-Lys-NHCH$_2$(pyridin-4-yl)

The title compound was prepared according to procedures already outlined in Example 18A except that Boc-Norleucine was substituted for Boc(N-im DNP)Histidine. This intermediate was then elaborated to the title compound according to procedures outlined in Example 18.

EXAMPLE 21

N-[3-(morpholin-4-yl)carbonyl-2(R)-benzylpropionyl]-His-ACHPA-Lys-NHCH$_2$(piperidin-4-yl)

N-[3-(morpholin-4-yl)carbonyl-2(R)-benzylpropionyl]-His-ACHPA-(N$^\epsilon$-CBZ)Lys-NHCH$_2$(pyridin-4-yl) was prepared according to procedures in Example 18 using 3-N-morpholinocarbonyl-2(R)-benzylpropionic acid prepared in Example 5. TLC (silica, 80:15:1 CHCl$_3$:MeOH:H$_2$O) Rf=0.33. MS, m/e=964(M+1). This material (0.3 gm) in MeOH (5 ml) and HCl (12N, 0.051 ml) with Pd/C 10% (0.15 gm) was hydrogenated (1 atm) for 24 hr. The reaction was subsequently filtered and evaporated in vacuo to give the title compound (0.2 gm). FAB mass spectral data: 836(M+1). NMR consistent with compound.

EXAMPLE 22

Ethyl (4-Phenyl-2(R,S)-Thioacetyl)butyrate

To a solution of (cabethoxymethylene)triphenylphosphorane (24 g, 68.9 mmol) in dry THF (200 ml) at room temperature, a solution of phenylacetaldehyde (5.38 g, 45 mmol) in dry THF (50 ml) was added, and the mixture was refluxed for 4 hours. The reaction was cooled, evaporated, and the residue was partitioned between ethylacetate (100 ml) and water. The organic layer was washed with water, dried ($MgSO_4$) and concentrated under reduced pressure to give an oil. The crude material was purified by MPLC on silica-gel using 5% ethylacetate in hexane to give two pure isomers of E (5.6 g) and Z (1.9 g) unsaturated esters. NMR ($CDCl_3$): 1.26(t, 3H), 3.51(d, 2H), 4.2(q, 2H), 5.83(dd, 1H), 7.08–7.41(m, 6H).

A solution of aforementioned unsaturated ester (E-isomer) (1.9 g, 10 mmol) in absolute ethanol (6 ml) was added to a solution of potassium thioacetate (1.26 g, 11 mmol) in ethanol (10 ml) and the mixture was stirred at room temperature overnight. The reaction mixture was concentrated in vacuo and residue was partitioned between ethylacetate (60 ml) and water. The organic phase was dried over $MgSO_4$ and evaporated to give product as a foam. The product was finally purified by flash chromatography on silica-gel.

EXAMPLE 23

N-[1-(RS)-ethoxycarbonyl-2-phenylethylsulfonyl]-His-ACHPA-Lys-NHCH$_2$(pyridin-4-yl)

Ethyl(4-phenyl-2(R,S)thioactyl)butyrate in $CCl_4$ (containing 10% ethanol) is reacted with a stream of $Cl_2$ gas at 0° C. for 2–3 hours. The solvent is removed under reduced pressure to give the corresponding sulfonyl chloride, which is reacted with His(DNP)-ACHPA-Lys(CbZ)-NHCH$_2$(pyridin-4-yl) to give fully protected peptide. The protecting groups are then removed as described in Examples 10 and 18 to give the title compound.

EXAMPLE 24

N-[(3-isopropylsulfonyl-2-benzylpropionyl]-His-ACHPA-NH-[N-methyl-quinucidinium-3-yl]⊕OAc⊖

To 15 ml dry degassed dimethylformamide (DMF) was added 931 mg (1.95 mmole) N$^\alpha$-t-butoxy-carbonyl-L-Histidyl-(3S,4S)-4-amino-5-cyclohexyl-3-hydroxy pentanoyl hydrazide, and the solution was cooled under a nitrogen atmosphere −30° C. with stirring. A freshly-prepared solution of HCl(g) in and tetrahydrofuran (4.56M, 4.28 ml, 19.5 mmole) was added to the cold reaction mixture adjusting the pH to within the desired range (0.5–1.5).

Isoamyl nitrite (287 μl, 2.15 mmole) was added in four positions at −20° to −18° C. over 2 to 3 hours while keeping the reaction mixture positive to a starch-potassium iodide paper test throughout. Upon complete formations of the acyl azide a precooled (−20° C.) slurry containing 3-(S)-aminoquinuclidine dihydrochloride (582 mg, 2.93 mmole) and triethylamine (3.00 μl, 23.4 mole), was added to the azide with stirring adjusting the pH of 9.0–9.5. The slurry was stirred vigorously at −20° C. for one hour then stored in the freezer overnight. The DMF was removed by rotavaporation and the residue was dissolved in 10 ml of chloroform:methanol:ammonia (CMA, 80:20:2), the insoluable solids were removed by filtration and the filtrate was loaded on to a Clark Still silica gel column (3.5 cmW×3.5 cm L, 2.30–4.00, 230–400 mesh Whatman G60). The product was eluted with CMA 80:20:2 in fractions 27 to 45 affording 875 mg (80% yield) of N$^\alpha$-t-butoxycarboxyl-L-Histidyl-(3S,4S)-4-amino-5-cyclohexyl-3-hydroxypentanoyl-3-quinuclidinyl amide after freeze-drying from dioxane.

Subsequent t-Boc deprotection using 50% trifluoroacetic acid/methylene chloride (R.T., 60 min.) afforded a quantitive yield of solid L-Histidyl-(3S,4S)-4-amino-5-cyclohexyl-3-hydroxypentanoyl-3-quinuclidinyl amide-tristrifluoroacetate salt, after trituration with fresh $Et_2O$ and filtration.

3-benzyl-2-(S)-isopropylsulfonylmethyl)propionic acid (166 mg, 0.615 mmol) was dissolved in 1.25 ml dry, degassed DMF of which N-hydroxysuccinimide (70.8 mg, 0.615 mmole) followed by dicyclohexylcarbodimide (1.23 mol 0.5MDCC/methylene chloride) were added. After stirring for 4 hours at room temperature under nitrogen and keeping the pH at 8.0 by adding triethylamine (100 μl, 0.782 mmole), the activated ester was reacted overnight with L-Histidyl-(3S,4S)-4-amino-5-cyclohexyl-3-hydroxypentanoyl 3-quinuclidinylamide.3TFA (368.5 mg, 0.535 mmole) pre-neutralized with diisopropylethylamine (270 μl, 1.61 mmole) in 3.00 ml DMF. After 17 hours the reaction mixture was concentrated and the residue chromatographed on an MPLC column 5.0 cmW×39 cm) with CMA, 85:15:1.5 element. The desired product eluted in fractions 68 to 98 affording 171 mg of 3-benzyl-2-(S)-(isopropyl sulfonylmethyl)propionyl-L-histidyl-(3S,4S)-4-amino-5-cyclohexyl 3-hydroxypentanoyl 3-quinuclidinyl amide. NMR (360 MHz) and FAB spectral analysis (M=+709)were consistent with the proposed structure. $IC_{50}=11$ nM.

Quaternization of the aforementioned amide (150 mg, 0.211 mmole) using methyl iodide (13.14 μl, 0.211 mmole) in 400 μl chloroform/100 μl DMF proceeded cleanly of the desired salt in 5 hours at room temperature. After lyophilizing the residue was dissolved in dilue acetic acid and passed through a column of Bio Rad AG3X4A (300 mg). After lyophilizing the eluate, the title compound was isolated (159.5 mg, 96% yield). FAB mass spec data (M/e): 725 (M+1). Elemental Analysis Calc'd: C 56.85, H 7.63, N 9.95 for $C_{38}H_{57}N_6O_6S + C_2H_3O_2^- C_2H_4O_2$ Found: C 99.17H 8.06N 9.51 NMR(360 Mhz): consistent with structure.

What is claimed is:

1. A peptide of the formula

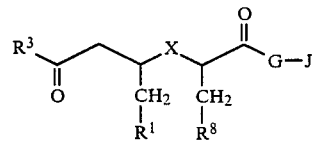

where:

R$^1$ is aryl, wherein aryl is unsubstituted or mono-, di- or trisubstituted phenyl or naphthyl where each substituent is independently selected from the group consisting of $C_1-C_8$-alkyl, amino, mono- or di-$C_1-C_4$-alkylamino, amino-$C_1-C_4$-alkyl, hydroxy-$C_1-C_4$-alkyl, mono- or di-$C_1-C_4$-alkylamino-$C_1-C_4$-alkyl, guanidyl, guanidyl-$C_1-C_4$-alkoxy, $CF_3$, halo, $CO_2H$, $CO_2-C_1-C_4$-alkyl, $NR^5R^6$, and $N(R^5)^+_3A^-$, wherein $R^5$ and $R^6$ are independently hydrogen, unsubstituted $C_1$–$C_4$-alkyl, and $A^-$ is an anion;

$R^3$ is aryl as defined above; Het where Het is a 5 to 7-membered monocyclic or 7 to 10-membered bicyclic ring containing one nitrogen atom; a Het as defined containing an additional heteroatom selected from N, NO, S, SO or $SO_2$; a substituted heterocyclic ring in which the heteroatoms are as defined and the substituent is on a ring carbon atom and selected from —OH, —$CO_2H$, —$CO_2$-$C_1$–$C_4$-alkyl, —$SO_3H$, —$SO_2NH_2$, aryl as defined above, —$CF_3$, -halo, or unsubstituted mono-, or di-$C_1$–$C_4$-alkylamino; a Het as defined containing a quaternary nitrogen atom; a quaternized ring as defined in which the nitrogen is substituted with one or two substituents where the first substituent is selected from $C_1$–$C_4$-alkyl, hydroxy-$C_1$–$C_4$-alkyl, —$CO_2H$, —$CO_2$-$C_1$–$C_4$-alkyl, —$SO_3H$, —$SO_2NH_2$, -aryl as defined above, —$CF_3$, -halo, or unsubstituted mono- or di-$C_1$–$C_4$-alkylamino, and the second substituent is $C_1$–$C_4$-alkyl; $NR^{20}R^{21}$ where $R^{20}$ and $R^{21}$ are independently selected from hydrogen, $C_1$–$C_4$-alkyl, aryl-$C_1$–$C_2$-alkyl or Het wherein Het and aryl are as defined above;

$R^4$ is $C_1$–$C_4$-alkyl or aryl-$C_1$–$C_2$-alkyl in which aryl is as defined above;

$R^8$ is $C_1$–$C_4$-alkyl, imidazol-4-yl, thiazol-5-yl, or aryl, as defined above;

$R^7$ and $R^{7a}$ are independently H, $C_1$–$C_7$-alkyl or $C_3$–$C_7$-cycloalkyl;

X is —$SO_2NH$—, —$SO_2CH_2$—, or —$SOCH_2$—;

G is:

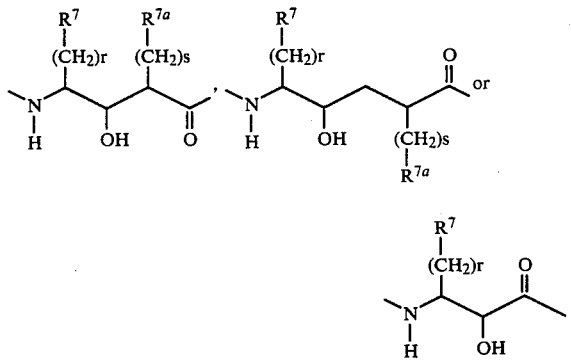

J is —Y—$(CH_2)_x$-[CH($R^5$)]$_y$-$(CH_2)_z$-$R^{10}$

Y is O, NH, or N-$C_1$–$C_4$-alkyl x is 0 to 1 y is 0 to 1 z is 0 to 4 s is 0 to 2

$R^5$ is as defined above $R^{10}$ is hydrogen; —OH; aryl as defined above; Het, as defined above; —$NH_2$; —$NR^{17}R^{18}$; —$NHR^{18}$; —$N(R^{17}R^{18}R^{19})^+A^-$, where $R^{17}$ and $R^{19}$ are independently $C_1$–$C_4$-alkyl, $R^{18}$ is aryl, Het or $C_1$–$C_4$-alkyl substituted with a substituent chosen from the group consisting of aryl, Het, —OH, —$NH_2$, —NH—$C_1$–$C_4$-alkyl, —N(-$C_1$–$C_4$-alkyl)$_2$, —$CO_2H$, or aryl, and $A^-$ in which aryl and $A^-$ are as defined above;

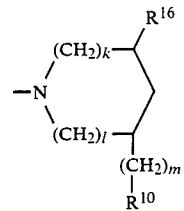

where k=1, 2; l=0, 1; $R^{16}$=—H, —OH, $C_1$–$C_4$-alkyl, aryl, or aryloxy wherein aryl is as defined; and $R^{10}$ is as defined above;

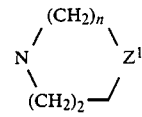

where k' and n=2 or 3; s'=1 or 2; $R^{10}$ is as defined above; and $Z^1$ is O, S, SO, $SO_2$, NH, $NR^{18}$ or $(N^+R^{17}R^{18})$ $A^-$ where $R^{17}$, $R^{18}$ and $A^-$ are defined above;

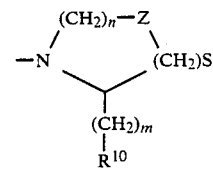

where k', s', $R^{10}$, and $Z^1$ are as defined above;
where t' is 2 or 3; k' is as defined above, and $Z^2$ is $NR^{18}$ or $N(R^{17}R^{18})^+A^-$, where $R^{17}$, $R^{18}$ and $A^-$ are as defined above;

or a pharmaceutically acceptable salt thereof.

2. A peptide according to claim 1 selected from the group consisting of:

N-[(2S-butyl-5-(morpholinocarbonyl)methyl-6-phenyl-4-thiahexanoyl-S,S-dioxide)]-ACHPA-NH-CH(2-butyl)-$CH_2$-(2-trimethylammoniomethylpyrrolidin-1-yl)$^+Cl^-$;

N-[(2S-butyl-5-(morpholinocarbonyl)methyl-6-phenyl-4-thiahexanoyl S,S-dioxide)];

N-[(2S-butyl-5-(morpholinocarbonyl)methyl-6-phenyl-4-thiahexanoyl-S,S-dioxide)]-ACHPA-NH-CH(2-butyl)-CH(OH)-$CH_2$-N($CH_3$)($CH_2CH_2$)$_2$O$^+Cl^-$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-$CH_2$-(pyridinium-1-yl)$^+Cl^-$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-$CH_2$-1-methylimidazolium-yl)$^+Cl^-$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-$CH_2$-N($CH_3$)$_2^+CH_2CH_2CO_2^-$;

N-[(2-(imidazol-4-yl)methyl-5-(morpholinocarbonyl)methyl-6-phenyl-4-thiahexanoyl-S,S-dioxide)]-ACHPA-NH-CH(2-butyl)-$CH_2$-N($CH_3$)$_2^+CH_2CH_2SO_3^-$;

N-[(2-(imidazol-4-yl)methyl-5-(morpholinocarbonyl)methyl-6-phenyl-4-thiahexanoyl-S,S-dioxide)]-

ACHPA-NH-CH(2-butyl)-CH$_2$-N(CH$_3$)$_2$+CH$_2$CH$_2$OHCl$^-$;

N-[(2-(imidazol-4-yl)methyl-5-(morpholinocarbonyl)-methyl-6-phenyl-4-thiahexanoyl-S,S-dioxide]-ACHPA-NH-CH(2-butyl)-CH$_2$-N(CH$_3$)$_2$+CH$_2$CH$_2$N(CH$_3$)$_2$Cl$^-$;

N-[(2-(imidazol-4-yl)methyl-5-(morpholinocarbonyl)-methyl-6-phenyl-4-thiahexanoyl-S,S-dioxide)]-ACHPA-NH-CH(2-butyl)-CH$_2$-NH-CH$_2$CH$_2$NH-C(=NH)-NH$_2$;

N-[(2-(imidazol-4-yl)methyl-5-(morpholinocarbonyl)-methyl-6-phenyl-4-thiahexanoyl-S,S-dioxide)]-Cal[CH(OH)CH$_2$]Val-NH-CH(2-butyl)-CH$_2$-NH-CH$_2$CH(NH$_2$)CO$_2$H;

N-[(2-(imidazol-4-yl)methyl-5-(morpholinocarbonyl)-methyl-6-phenyl-4-thiahexanoyl-S,S-dioxide)]-AmACHPA-NH-CH(2-butyl)-CH$_2$-NH-CH$_2$CH(CO$_2^-$)N(CH$_3$)$_3$+;

N-[(2-(imidazol-4-yl)methyl-5-(morpholinocarbonyl)methyl-6-phenyl-4-thiahexanoyl-S,S-dioxide)]-Cal[CH(OH)CH$_2$]Val-N(i-butyl)-CH$_2$-CH$_2$-N(CH$_2$CH$_2$)$_2$N(CH$_3$)$_2$+Cl$^-$;

N-[(2-(imidazol-4-yl)methyl-5-(morpholinocarbonyl)-methyl-6-phenyl-4-thiahexanoyl-S,S-dioxide)]-(2S-i-butyl)-ACHPA-NH-CH(2-butyl)-CH$_2$-NH-CH$_2$(pyridin-4-yl N-oxide);

N-[(2-(imidazol-4-yl)methyl-5-(morpholinocarbonyl)-methyl-6-phenyl-4-thiahexanoyl-S,S-dioxide)]-(2S-allyl)ACHPA-NH-CH(2-butyl)-CH$_2$-NH-CH$_2$(pyridin-2-yl N-oxide);

N-[(2-(imidazol-4-yl)methyl-5-(morpholinocarbonyl)-methyl-6-phenyl-4-thiahexanoyl-S,S-dioxide]-Cal[CH(NH$_2$)CH$_2$]-Val-NH-CH(2-butyl)-CH$_2$-NH-CH$_2$(pyridin-2-yl-N-oxide);

N-[(2-butyl-5-(morpholinocarbonyl)methyl-6-phenyl-4-thiahexanoyl-S,S-dioxide)]-Cal(CH(OH)CH$_2$)Val-NH-2(S)-methylbutyl.

3. A composition comprising a therapeutically-effective amount of a peptide according to claim 1, and a pharmaceutical carrier.

4. A method of treating renin-associated hypertension or renin-associated congestive heart failure comprising administering to a patient in need of such treatment, a therapeutically-effective amount of a peptide according to claim 1.

5. A method according to claim 4, wherein the patient is a human and the therapeutically-effective amount is from 0.1 to 40 grams per day.

* * * * *